United States Patent
Ikeda et al.

(10) Patent No.: US 6,809,190 B2
(45) Date of Patent: Oct. 26, 2004

(54) FUNCTIONAL PEPTIDE NUCLEIC ACID AND ITS PRODUCTION METHOD

(75) Inventors: Hisafumi Ikeda, Chiba (JP); Madoka Tonosaki, Saitama (JP)

(73) Assignee: Credia Japan Co., Ltd., Kyoto (JP)

(*) Notice: Subject to any disclaimer, the term of this patent is extended or adjusted under 35 U.S.C. 154(b) by 0 days.

(21) Appl. No.: 10/422,285

(22) Filed: Apr. 24, 2003

(65) Prior Publication Data

US 2003/0229201 A1 Dec. 11, 2003

(51) Int. Cl.[7] ........................ C07H 21/00; C07H 21/02; C07H 21/04
(52) U.S. Cl. ..................... 536/23.1; 536/25.3; 536/26.6
(58) Field of Search .............................. 536/23.1, 25.3, 536/26.6

(56) References Cited

PUBLICATIONS

Kisfaludy et al. Synthesis 1983, (4) pp. 325–327.*
Armitage, Bruce et al, Peptide Nucleic Acid (PNA)/DNA Hybrid Duplexes: Intercalation by an Internally Linked Anthraquinone, *Nucleic Acids Research*, 1998, vol. 26, No. 3, pp 715–720.
Dueholm, Kim L. et al, Synthesis of Peptide Nucleic Acid Monomers Containing the Four Natural Nucleobases: Thymine, Cytosine, Adenine, and Guanine and their Oligomerization, JOC 1994, vol. 59, pp 5767–5773.
Egholm, Michael et al, Peptide Nucleic Acids (PNA), Oligonucleotide Analogues with an Achiral Peptide Backbone, *J. Am. Chem. Soc.* 1992, vol. 114, pp 1895–1897.
Egholm, Michael et al, Recognition of Guanine and Adenine in DNA by Cytosine and Thymine Containing Peptide Nucleic Acids (PNA), *J. Am. Chem. Soc.* 1992, vol. 114, pp 9677–9678.
Hanvey, Jeffery C. et al, Antisense and Antigene Properties of Peptide Nucleic Acids, *Science*, vol. 258, Nov. 27, 1992, pp 1481–1485.
Lohse, Jesper et al, Fluorescein–Conjugated Lysine Monomers for Solid Phase Synthesis of Fluorescent Peptides and PNA Oligomers, *Bioconjugate Chem.*, vol. 8, 1997, pp 503–509.
Nielson, Peter E. et al, Sequence–Selective Recognition of DNA by Strand Displacement with a Thymine–Substituted Polyamide, *Science*, vol. 254, Dec. 6, 1991, pp. 1497–1500.
Thomson, Stephen A. et al, Fmoc Mediated Synthesis of Peptide Nucleic Acids, *Tetrahedron*, vol. 51, No. 22, 1995, pp 6179–6194., 1995.

* cited by examiner

*Primary Examiner*—Jezia Riley
(74) *Attorney, Agent, or Firm*—Richard M. Goldberg

(57) ABSTRACT

A novel method for synthesizing functional PNA having superior cost performance and which enables functional molecules to be introduced extremely rapidly, and compounds used therein. Disclosed is a method for producing a functional PNA oligomer; wherein a PNA monomer unit having adenine, guanine, cytosine or thymine protected by a protecting group is reacted with Fmoc-ω-amino acid-$^{Boc}$PNA-OH, and after synthesizing PNA oligomer, a functional molecule having free carboxylic acid is introduced into that PNA oligomer followed by deprotecting the protecting group; compounds synthesized by the method; and, Fmoc-ω-amino acid-$^{Boc}$PNA-OH that functions as a precursor PNA monomer unit.

26 Claims, 1 Drawing Sheet

Negatively charged

DNA

Peptide nucleic acid (PNA)

Neither negatively or positively charged

Fmoc type PNA monomer unit        Boc type PNA monomer unit

FUNCTIONAL PEPTIDE NUCLEIC ACID AND ITS PRODUCTION METHOD

BACKGROUND OF THE INVENTION

The present invention relates to a novel method for producing a functional peptide nucleic acid monomer, a functional peptide nucleic acid oligomer produced by that method, and its intermediates. More particularly, the present invention relates to a production method comprising introducing one type or two or more types of a functional molecule post-synthetically following introduction of a precursor PIVA monomer unit into a PNA oligomer.

Nucleic acids consist of DNA and RNA that govern the genetic information of living organisms. In contrast, peptide nucleic acids (PNA) refers to modified nucleic acids in which the sugar phosphate skeleton of a nucleic acid has been converted to an N-(2-aminoethyl)glycine skeleton (FIG. 1). Although the sugar-phosphate skeletons of DNA/RNA are subjected to a negative charge under neutral conditions resulting in electrostatic repulsion between complementary chains, the backbone structure of PNA does not inherently have a charge. Therefore, there is no electrostatic repulsion. Consequently, PNA has a higher ability to form double strands as compared with conventional nucleic acids, and has a high ability to recognize base sequences. Moreover, since PNA is extremely stable with respect to nucleases and proteases in the living body and is not decomposed by them, studies are being conducted on its application to gene therapy as an antisense molecule.

As a result of using PNA in technology that conventionally used DNA as a medium, it has become possible to compensate for those shortcomings of DNA that were heretofore unable to be overcome. For example, PNA can be applied to "DNA microarray technology" for rapid and large-volume systematic analysis of genetic information, as well as recently developed "molecular beacons" used a probes capable of detecting that a base sequence has been specifically recognized using emission of fluorescent light. Since both of these use DNA lacking enzyme resistance as the medium, strict sampling is required when using these technologies. The satisfying of this requirement is the key to achieving greater sophistication of these technologies.

On the other hand, since PNA is completely resistant to enzymes, by substituting the use of DNA for PNA in DNA microarray technology and molecular beacons, the previously mentioned technical shortcomings can be overcome, leading to expectations of being able to take further advantage of the merits of these technologies.

Although there are many other fields in which the use of PNA is expected to lead to further advancements in addition to DNA microarray technology and molecular beacons, in these fields it will be necessary to design novel PNA monomers by enabling PNA to function efficiently, namely by realizing the efficient introduction of functional molecules into PNA monomers.

Since ordinary solid-phase peptide synthesis methods are used for PNA oligomer synthesis methods, classification of PNA monomer units according to PNA backbone structure yields the two types consisting of Fmoc type PNA monomer units and tBoc type PNA monomer units (FIG. 2).

Methods for synthesizing Fmoc type PNA monomer units have already been established, and since their oligomer synthesis can be carried out using an ordinary DNA automated synthesizer, synthesis can be carried out on a small scale by the following route:

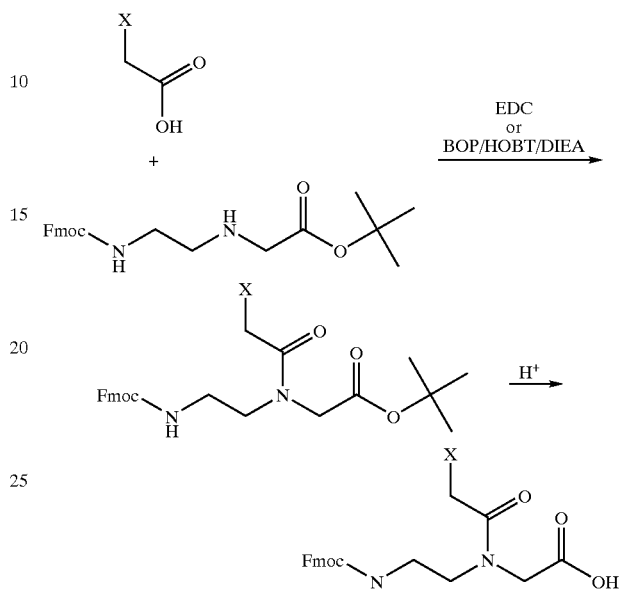

Stephen A. Thompson, John A. Josey, et. al, *Tetrahedron* 1995, 51, 6179–6194.

(wherein X represents guanine, thymine, cytosine or adenine).

Initially, tBoc type PNA monomer units like those shown below:

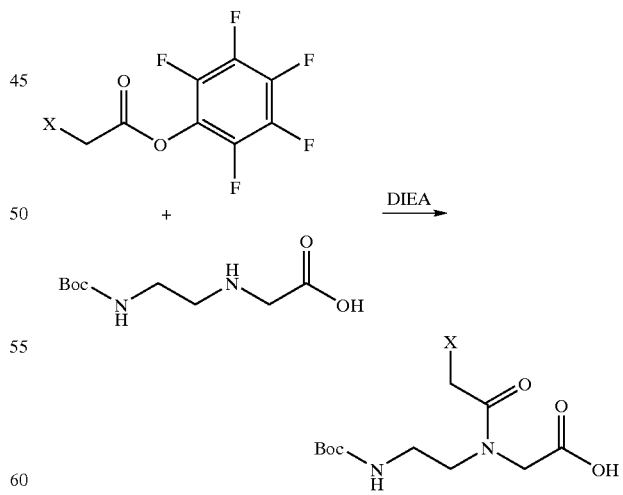

Michael Egholm, Ole Buchardt, Peter E. Nielsen, and Rolf H. Berg *J. Am. Chem. Soc.* 1992, 114, 1895–1897.

were used and this was followed by the establishment of more efficient synthesis methods.

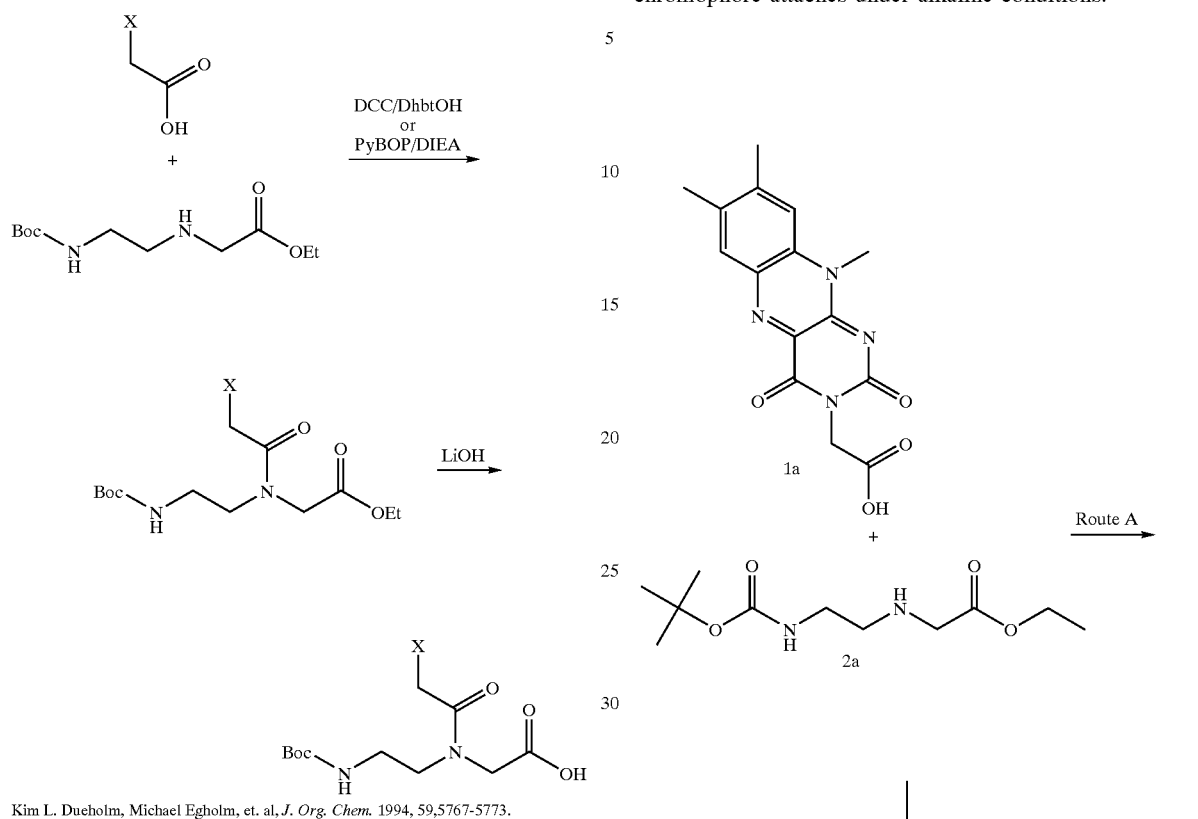

Kim L. Dueholm, Michael Egholm, et. al, *J. Org. Chem.* 1994, 59, 5767-5773.

However, since the previously mentioned Fmoc type was developed that offered easier handling, the frequency of use of the tBoc type is decreasing.

However, when introducing a functional molecule other than the four types of nucleic acid bases of guanine, thymine, cytosine and adenine, such as when introducing a photofunctional molecule, there are many cases in which the functional molecule to be introduced is unstable under alkaline conditions, and thus a tBoc type of PNA backbone structure that is not used under alkaline conditions is highly useful. A patent application for a "method for producing t-butoxycarbonyl-aminoethylamine and amino acid derivatives" has already been made by the inventors of the present invention as Japanese Patent Application No. 2000-268638.

In addition, there are also five examples of synthesis of monomer units of photofunctional oligo PNA in the prior art. Although all of these use the above route, their yields are either not described or are extremely low (Peter E. Nielsen, Gerald Haaiman, Anne B. Eldrup PCT Int. Appl. (1998) WO 985295 A1 19981126, T. A. Tran, R.-H. Mattern, B. A. Morgan (1999) J. Pept. Res, 53, 134–145, Jesper Lohse et al. (1997) Bioconjugate Chem., 8, 503–509, Hans-georg BAtz, Henrik Frydenlund Hansen, et al. Pct Int. Appl. (1998) WO 9837232 A2 19980827, Bruce Armitage, Troels Koch, et al. (1998) Nucleic Acid Res., 26, 715–720). In addition, since the structures of the compounds used have the characteristic of being comparatively stable under alkaline conditions, they are expected to be uable to be produced in good yield using a method similar to the above-mentioned methods of the prior art, namely the following route A, if an unstable chromophore attaches under alkaline conditions.

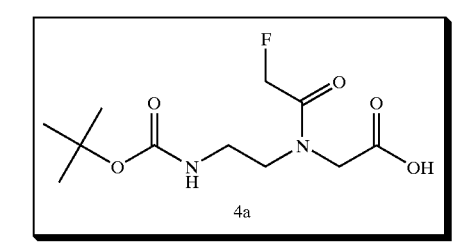

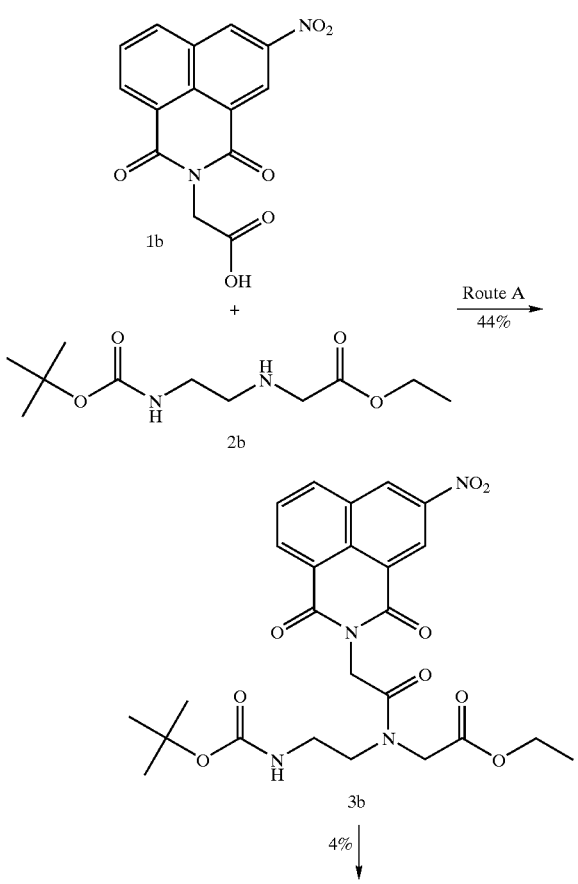

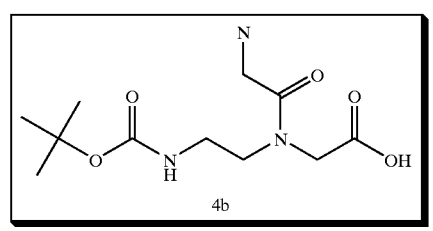

Thus, since there are typically many cases in which photofunctional molecules or other functional molecules are expensive, methods for synthesizing more pertinent functional PNA, namely methods for extremely rapidly introducing these functional molecules for (1) efficient introduction of functional molecules into a PNA backbone structure in the design of functional PNA monomer units, (2) synthesis routes in consideration of cost performance, and (3) adaptation to applications as gene diagnostic drugs, have been sought.

In consideration of the above problems, the inventors of the present invention found a novel method for producing functional PNA monomers consisting of synthesizing a photofunctional PNA monomer 4 nearly quantitatively by using a t-butoxycarbonylaminoethylamine derivative 6 for the PNA backbone structure, and condensing with an active ester form 5 containing the pentafluorophenyl group of 1 as indicated in the following route B.

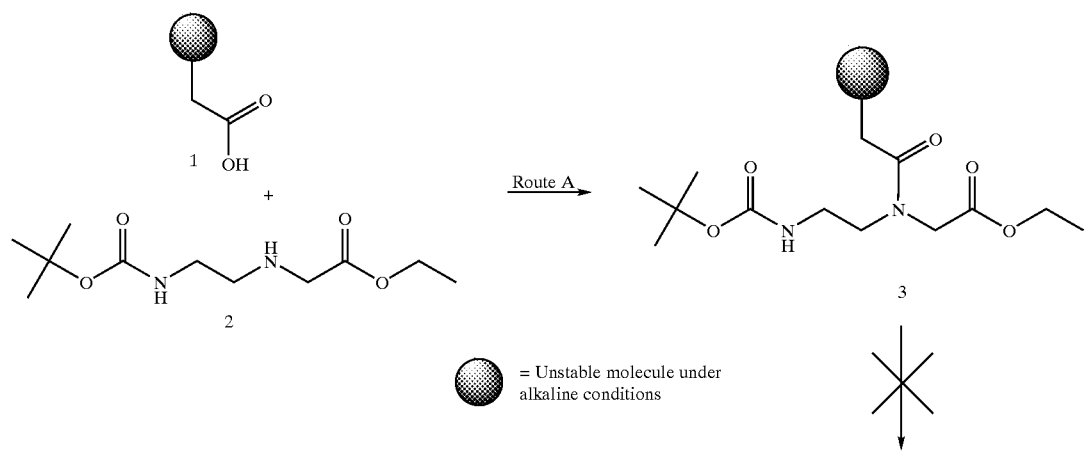

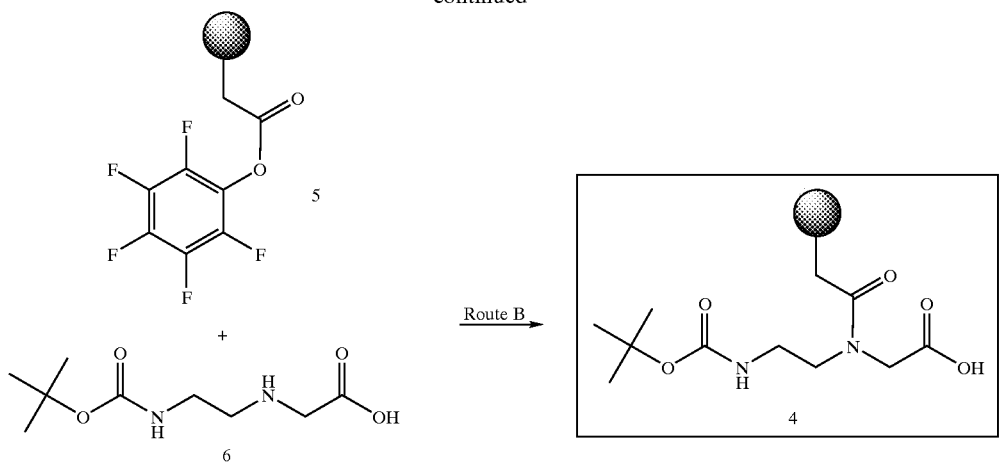

In addition, the inventors of the present invention found a different method for synthesizing functional PNA monomers by using a benzyloxycarbonyl-ω-amino acid derivative instead of the above t-butoxycarbonylaminoethylamine derivative 6 for the PNA backbone structure (route C). Patent applications have already been made for these methods.

Thus, methods for ultimately synthesizing functional PNA are being established industrially that consist of synthesizing functional PNA monomers according to methods using either of the above routes B or C, followed by polymerization of those monomers. Namely, it is becoming possible to industrially synthesize large volumes of functional PNA used as PNA probes using existing functional PNA synthesis methods.

On the other hand, improvements are also being made on methods for producing functional PNA for the purpose of improving cost performance and allowing ultra-high-speed introduction of functional molecules. For example, a method has been reported in which functional molecules are introduced into PNA oligomers post-synthetically by using the following precursor PNA monomer unit as a different approach from the method described above using functional PNA monomer units (Oliver Seitz: Tetrahedron Letters 1999, 40, 4161–4164).

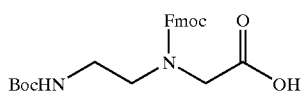

In this method, after introducing the above precursor PNA monomer unit into a PNA oligomer, functional PNA is synthesized by additionally introducing a functional molecule.

However, this method has the disadvantage of there being limitations on the types of functional molecules that can be introduced.

For example, as indicated below, the commercially available photofunctional molecule, succinimide ester, is unable to be introduced. Although it is necessary to first introduce a linker such as Fmoc-Gly in order to introduce this photofunctional molecule, the above compound becomes difficult to use as a result of this.

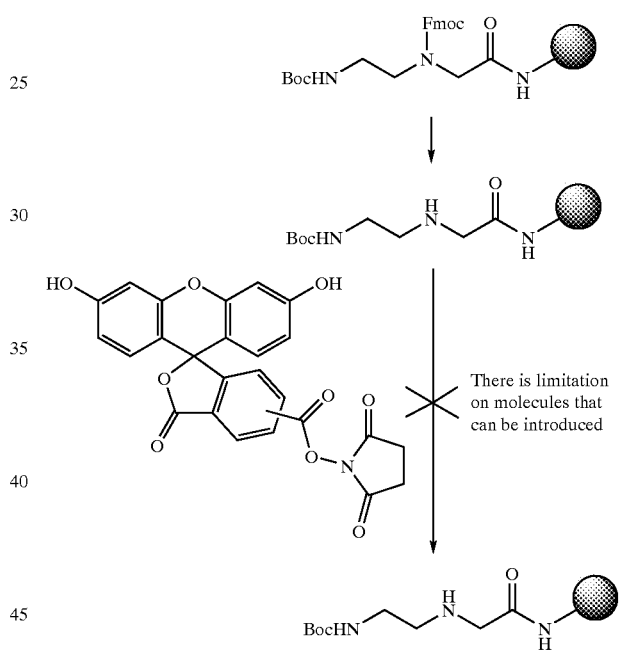

In addition, although DNA oligomers, RNA oligomers and PNA oligomers have been used in the past as fluorescent probes for introducing into cells, in order to introduce these into cells, they must naturally be able to pass through the cell membrane. However, since the surface of the cell membrane has a negative charge, it is extremely difficult to introduce DNA/RNA oligomers that are inherently negatively charged.

On the other hand, although PNA oligomers are electrically neutral, results have been obtained which indicate they are difficult in permeating the cell membrane. Thus, when introducing PIVA oligomers into a cell, that introduction must be facilitated by pretreating the membrane surface, or they must be introduced by using a transfection reagent.

However, in the case of introducing PNA oligomers by performing such treatment, even though the probe's function may be demonstrated, there is no guarantee that the behavior inherently demonstrated by the living body will always be accurately represented. Moreover, this is only true in the case of one cell, and in the case of numerous cells (individual body), their use is practically impossible.

On the basis of this current situation and viewpoint, the development of a fluorescent PNA probe having a membrane permeation function is considered to be useful.

It should be noted that fluorescent PNA probes having a membrane permeation function already exist. Examples include (1) a fluorescent PNA probe in which an oligopeptide having a membrane permeation function is linked to PNA, and (2) a fluorescent PNA probe in which a phospholipid having a membrane permeation function is linked to PNA. However, the portion of these probes other than the PNA is expected to be decomposed by enzymes such as proteases within cells after they have permeated the cell membrane, thereby causing them to be retained within the cell. Since this leads to excess PNA probes that were unable to capture the target losing their membrane permeation function and having difficulty in moving outside the cell in subsequent washing steps, this means that the gene expression system inherently possessed by the cell cannot be expressed accurately.

Thus, it is an object of the present invention to provide a novel method for synthesizing functional PNA having superior cost performance and which enables functional molecules to be introduced extremely rapidly, compounds used therein, and novel functional PNA.

SUMMARY OF THE INVENTION

As a result of extensive research in consideration of the above problems, the inventors of the present invention surprisingly found that, by optimizing the structure of precursor PNA monomer units, the above problems of the prior art can be overcome, and functional PNA can be synthesized over an extremely wide range, thereby leading to completion of the present invention.

CONSTRUCTION OF THIS INVENTION

More specifically, an aspect of the present invention relates to a method for producing a functional PNA oligomer, wherein a PNA monomer unit having adenine, guanine, cytosine or thymine protected by a protecting group is reacted with Fmoc-ω-amino acid-$^{Boc}$PNA-OH represented by the following general formula (I):

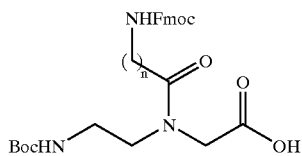

(wherein n represents an plus integer)

and after synthesizing PNA oligomer, a functional molecule having free carboxylic acid is introduced into that PNA oligomer followed by deprotecting of the protecting group.

Further, the present invention relates to the method described above, wherein the Fmoc-ω-amino acid-$^{Boc}$PNA-OH is produced by a reaction between Fmoc-ω-amino acid pentafluorophenyl ester and $^{Boc}$PNA-OH.

Further, the present invention relates to the method described above, wherein the Fmoc-ω-amino acid pentafluorophenyl ester is produced by a reaction between Fmoc-ω-amino acid and pentafluorophenol.

Further, the present invention relates to the method described above, wherein different functional molecule is introduced after introducing a functional molecule.

Still further, the present invention relates to the method described above, wherein the introduced functional molecule is chosen from a photofunctional molecule, a membrane-permeable functional molecule, an organ-selective functional molecule, a bactericidal functional molecule and a molecule-recognizing functional molecule.

Further, the present invention relates to the method described above, wherein the introduced functional molecule contains a photofunctional molecule and a membrane-permeable functional molecule.

In addition, the present invention relates to the method described above, wherein the photofunctional molecule is FITC, ROX, TAMRA or Dabcyl, and the membrane-permeable functional molecule is a water-soluble amino acid.

In addition, the present invention relates to the method described above, wherein the protecting group that protects adenine, guanine, cytosine or thymine is a Z group.

In addition, the present invention relates to the method described above, wherein synthesis of PNA oligomer contains condensation and elongation in a PNA chain using a solid-phase carrier for the tBoc method.

In addition, the present invention relates to the method described above, wherein the solid-phase carrier for the tBoc method is MBHA.

In addition, the present invention relates to the method described above, wherein introduction of a functional molecule having free carboxylic acid is carried out by dehydration condensation with a primary amino group obtained by selectively deprotecting the Fmoc group by piperidine treatment, In addition, the present invention relates to the method described above, wherein Fmoc-ω-amino acid-$^{Boc}$PNA-OH is a compound represented by the following general formula (I):

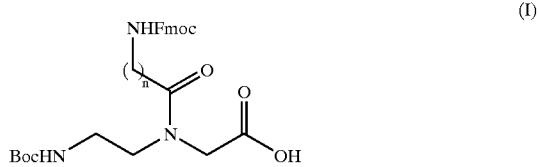

(wherein n represents an integer of 1 through 15).

In addition, the present invention relates to the method described above, the method comprising one or more of the following steps a) through d) of:

a) reacting Fmoc-ω-amino acid and pentafluorophenol in a step in which Fmoc-ω-amino acid pentafluorophenylester is produced;

b) introducing Fmoc-ω-amino acid into $^{Boc}$PNA-OH by reacting Fmoc-ω-amino acid pentafluorophenyl ester with $^{Boc}$PNA-OH in a step in which Fmoc-ω-amino acid-$^{Boc}$PNA-OH is produced;

c) producing PNA oligomer by reacting a PNA monomer unit with Fmoc-ω-amino acid-$^{Boc}$PNA-OH in a step in which PNA oligomer is produced from Fmoc-ω-amino acid-$^{Boc}$PNA-OH; and, d) carrying out introduction of a functional molecule into PNA oligomer by dehydration condensation of a primary amino group obtained by selectively deprotecting an Fmoc group by piperidine treatment in a step in which a functional PNA oligomer is produced from the above PNA oligomer.

In addition, an aspect of the present invention relates to a compound represented by the following general formula (I):

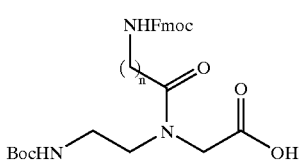

(I)

(wherein n represents an integer of 1 through 15).

In addition, the present invention relates to a method for producing the compound represented by general formula (I):

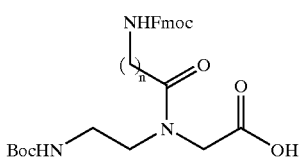

(I)

(wherein n represents an integer of 1 through 15), the method comprising the introduction of Fmoc-ω-amino acid by reacting Fmoc-ω-amino acid with pentafluorophenol, and reacting that reaction product with $^{Boc}$PNA-OH.

In addition, the present invention relates to a compound represented by the following general formula (II):

In addition, the present invention relates to the compound described above, wherein R or $R^1$ represents a cell membrane-permeable functional molecule derivative.

In addition, the present invention relates to the compound described above, wherein $R^1$ represents a functional carboxylic acid derivative.

In addition, the present invention relates to the compound described above, wherein $X_1 = Z_1 = 1$.

In addition, the present invention relates to the compound described above, wherein $Y_1 \geq 2$ and $Z_2 = 1$.

In addition, the present invention relates to the compound described above, wherein $a \leq 6$, $b \leq 4$ and $f \leq 6$.

In addition, the present invention relates to the compound described above, wherein $R^1$ is a photofunctional carboxylic acid derivative.

Further, the present invention relates to a compound described above, represented by the following general formula (III):

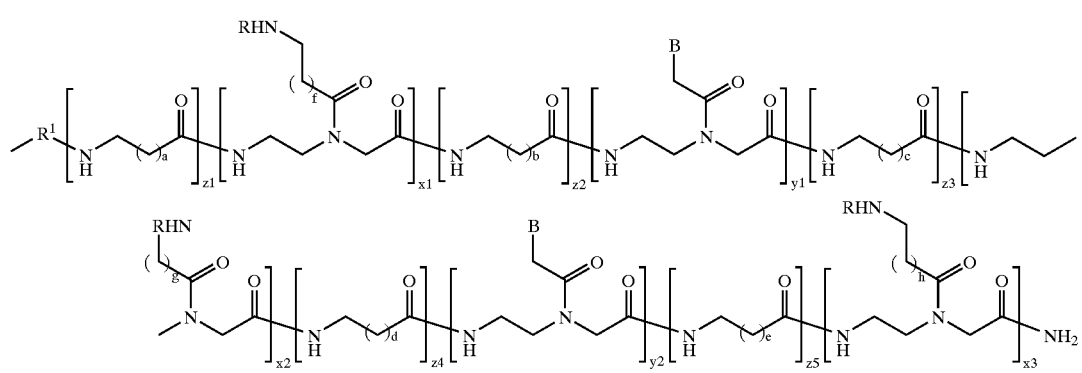

(II)

(wherein B's each independently are the same or different and represent adenine, guanine, cytosine or thymine, R's each independently are the same or different and represent an Fmoc group or a functional carboxylic acid derivative, $R^1$ represents a hydrogen atom or a functional carboxylic acid derivative, a through h represent integers of 0 to 10, $X_1$ through $X_3$, $Y_1$, $Y_2$ and $Z_1$ through $Z_5$ all represent integers of 0 or more, $X_1+X_2+X_3 \geq 0$, $Y_1+Y_2 > 0$, and $Z_1+Z_2+Z_3+Z_4+Z_5 \geq 0$, provided that $X_1+X_2+X_3$ and $Z_1+Z_2+Z_3+Z_4+Z_5$ are not simultaneously 0, and in the case where $X_1+X_2+X_3=0$, $R^1$ is a functional carboxylic acid derivative).

In addition, the present invention relates to the compound described above, wherein $Z_1+Z_2+Z_3+Z_4+Z_5=0$, and $R^1$ is a hydrogen atom.

In addition, the present invention relates to the compound described above, wherein R includes a carboxylic acid derivative of methyl red.

In addition, the present invention relates to the compound described above, wherein $X_1+X_2+X_3=9$, and $Y_1+Y_2=1$.

In addition, the present invention relates to the compound described above, wherein $X_1=3$, $X_2=6$ and $Y_1=1$.

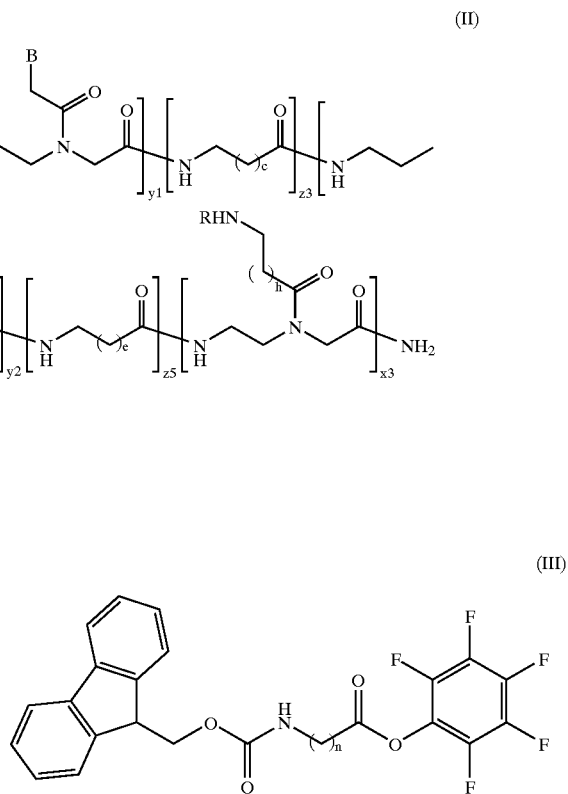

(III)

(wherein n represents an integer of 1 through 15).

In addition, the present invention relates to the method for producing the compound represented by the following general formula (III):

(III)

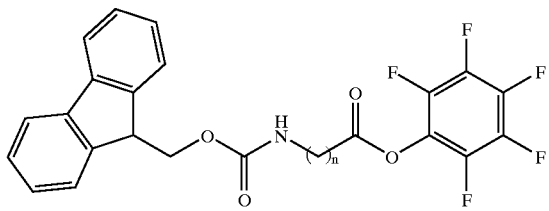

(wherein, n represents an integer of 1 through 15), wherein Fmoc-ω-amino acid is reacted with pentafluorophenol.

The present invention succeeds in being able to synthesize photofunctional PNA oligomers nearly quantitatively by introducing a precursor PNA monomer unit, in which Fmoc-ω-amino acid has been introduced into a PNA backbone structure, namely Fmoc-ω-amino acid-$^{Boc}$PNA-OH, into a PNA oligomer, followed by post-synthetically introducing a functional molecule.

According to the above characteristics, in the production method of the present invention, it is not necessary to use commercially available succinimide ester for the functional molecule to be introduced, but rather provided a compound has a carboxyl group, that compound can be used without problem and introduced quantitatively. Consequently, the production method according to the present invention has extremely superior cost performance.

In addition, by dividing the resin after introducing the precursor PNA monomer units into functional PNA oligomer, different functional molecules can be introduced into each resin. Thus, according to the production method of the present invention, an extremely rapid functional PNA oligomer synthesis procedure can be developed.

An example of a functional PNA oligomer that can be efficiently synthesized by the method of the present invention is the compound represented by the following general formula (II):

$R^1$ is a functional carboxylic acid derivative), wherein $Z_1+Z_2+Z_3+Z_4+Z_5=0$ and $R^1$ is a hydrogen atom.

According to the present invention, identical or different functional molecules can be introduced at a plurality of arbitrary sites in the compound represented by the above-mentioned general formula (II). Namely, although piperidine treatment and post-synthetic introduction of a functional molecule can be carried out collectively after introducing a PNA oligomer using the previously mentioned precursor PNA monomer units, this is indispensable in terms of rapidly designing antenna pedia that improve the cell membrane permeation function of PNA oligomers. The method according to the present invention is extremely superior with respect to this point as well.

An example of a compound produced in this manner is a compound in which $Z_1+Z_2+Z_3+Z_4+Z_5>0$, R represents a cell membrane-permeable molecule derivative, and $R^1$ represents a functional carboxylic acid derivative in the previously mentioned general formula (II).

This probe can be broadly divided into three regions consisting of fluorescent-labeled region, cell membrane permeation function region, and molecule-recognizing region, and has a form in which each of these are linked by means of linker sites (section represented by the suffixes of $Z_1$ through $Z_5$).

Both commercially available products as well as a novel fluorescent-labeled PNA monomer unit for which PCT application has already been filed by the inventors of the present invention may be used for the fluorescent-labeled compound.

The molecule recognition site is synthesized using a commercially available PNA unit. This is characterized by the use of a novel PNA unit represented by general formula (I) for which a patent application has already been made in Japan for the membrane permeation function region. This novel PNA unit represented by general formula (I) is a precursor unit developed for post-synthetic introduction of functional molecules, and is characterized by allowing the collective introduction of molecules having the same func- (II)

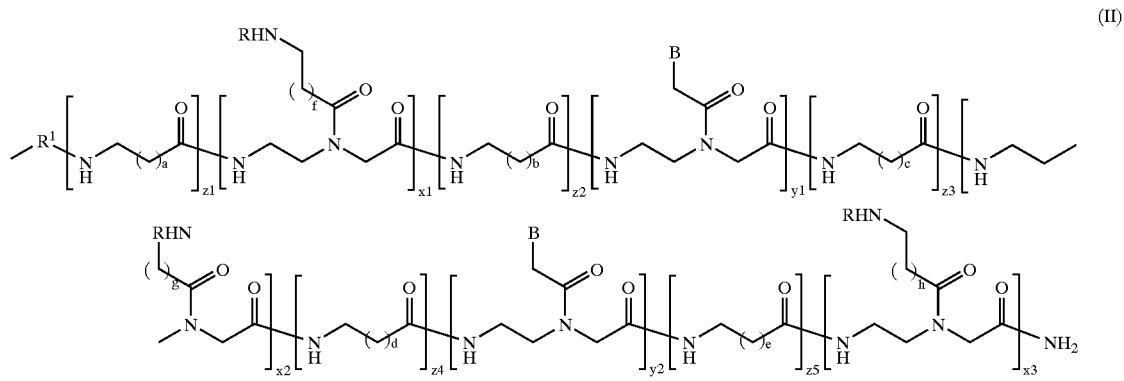

(wherein B's each independently are the same or different and represent adenine, guanine, cytosine or thymine, R's each independently are the same or different and represent an Fmoc group or a functional carboxylic acid derivative, $R^1$ represents a hydrogen atom or a functional carboxylic acid derivative, a through h represent integers of 0 to 10, $X_1$ through $X_3$, $Y_1$, $Y_2$ and $Z_1$ through $Z_5$ all represent integers of 0 or more, $X_1+X_2+X_3 \geq 0$, $Y_1+Y_2>0$, and $Z_1+Z_2+Z_3+Z_4+Z_5 \geq 0$, provided that $X_1+X_2+X_3$ and $Z_1+Z_2+Z_3+Z_4+Z_5$ are not simultaneously 0, and in the case where $X_1+X_2+X_3=0$, tion as was previously mentioned after introducing a plurality of these novel PNA units in a row.

Thus, according to the present invention, various functional molecules, without being limited to photofunctional molecules, can be both easily and extremely efficiently introduced into PNA.

Examples of such functional molecules include naphthalimide, flavin, dabcyl, biotin, FAM, rhodamine, TAMRA, ROX, HABA, pyrene and coumarine-type photofunctional monomer units, membrane-permeable functional molecules, organ-selective functional molecules, bactericidal functional molecules and molecule-recognizing functional molecules.

Namely, the term "functional" in the present invention is not limited to photofunctionality, but also refers to all types of functions newly imparted to compounds by a certain modification, including membrane permeability, organ selectivity, bactericidal function and molecule recognition function.

Moreover, the term "functional PNA" in the present invention not only refers to the direct linkage of PNA monomers by a 2-(N-aminoethyl)glycine skeleton, but also to those containing a hydrocarbon chain and so forth in the form of a linker between them.

Other aspects and advantages of the invention will become apparent from the following description, taken in conjunction with the accompanying drawings, illustrating by way of example the principles of the invention.

DETAILED DESCRIPTION OF THE INVENTION

Figure 1:
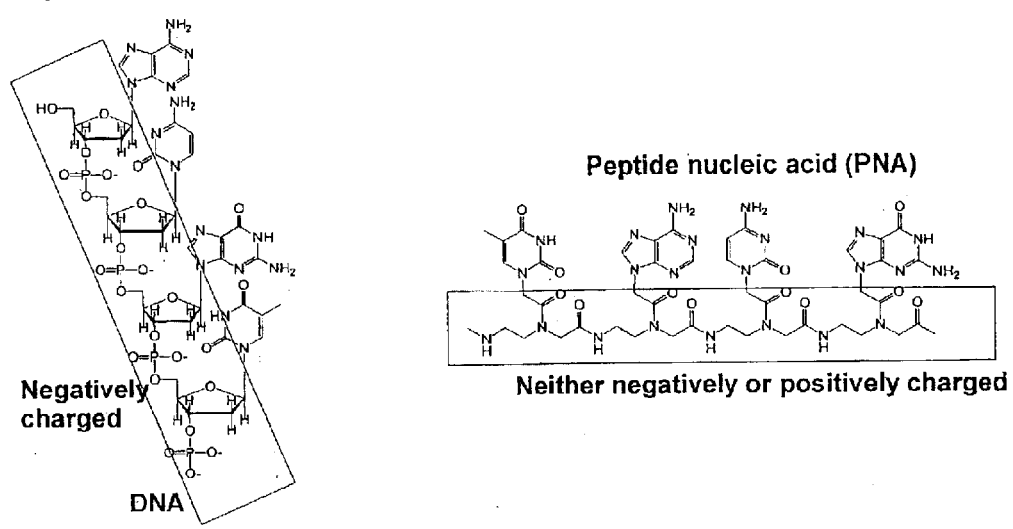
FIG. 1 shows the difference of the structure and the electric charge between DNA and PNA.
Figure 2:
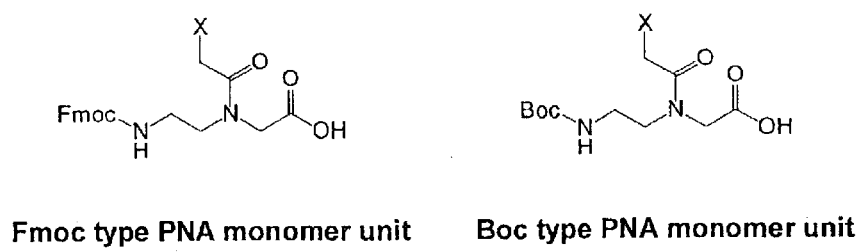
FIG. 2 shows the structures of two PNA monomer units.

The following provides a more detailed explanation of the characteristics of the method according to the present invention.

The synthesis route of the oligo PNA according to the present invention is typically as indicated below.

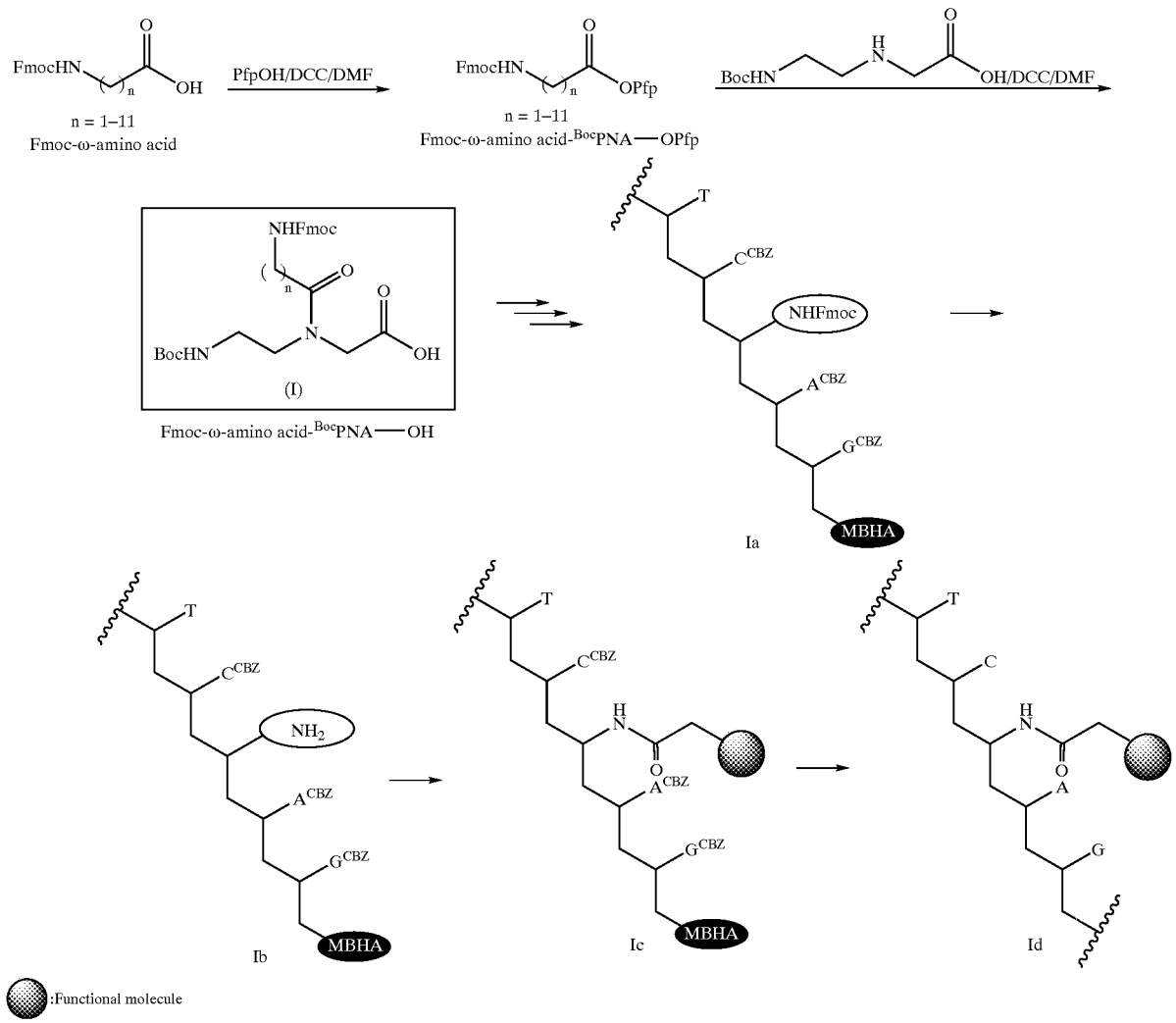

Wherein MBHA means methylbenzhydrylamine resin, and used for synthesizing peptide by solid-phase Boc method.

First, as indicated below, Fmoc-ω-amino acid and pentafluorophenol (PfpOH) are allowed to react as necessary, and Fmoc-ω-amino acid-$^{Boc}$PNA-OH is synthesized from the resulting Fmoc-ω-amino acid pentafluorophenyl ester (Fmoc-ω-amino acid-OPfp).

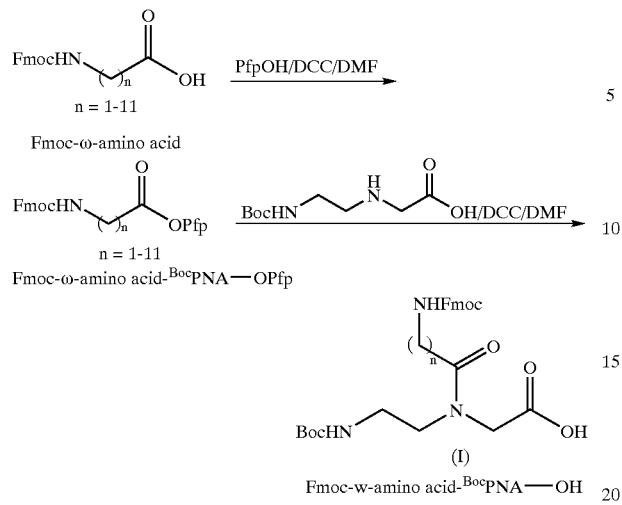

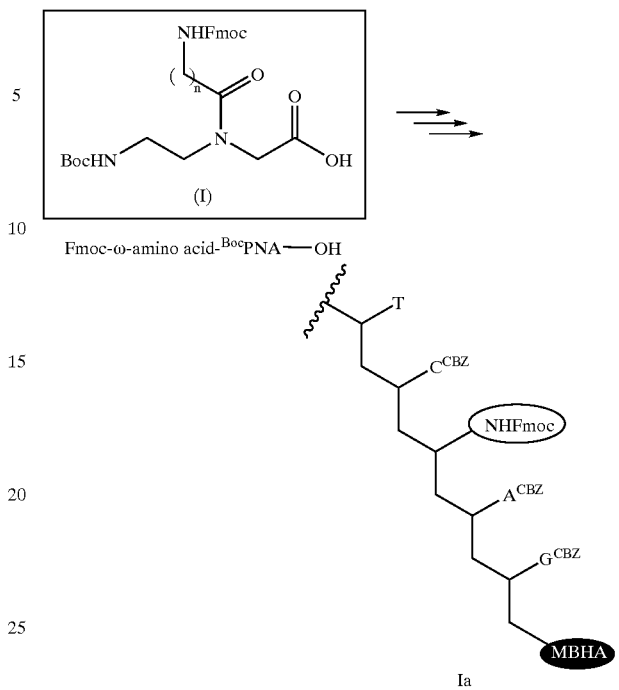

Fmoc-ω-amino acid-$^{Boc}$PNA—OH

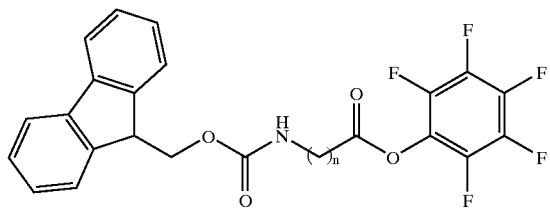

In order to obtain a solution of the Fmoc-ω-amino acid-OPfp that is used in the following steps, either an organic solvent such as DMF or a water-soluble solvent containing acetone and water, for example, can be used preferably. In the case of using the above water-soluble solvent, it offers advantages in terms of post-treatment such as purification.

The above Fmoc-ω-amino acid-OPfp is obtained as represented by, for example, the following formula (III):

(III)

(wherein n is an integer of 0 to 15) by reacting Fmoc-ω-amino acid and PfpOH in a DMF solution while adding DCC.

Next, a DMF solution of $^{Boc}$PNA-OH and diisopropylethylamine are added to this to obtain Fmoc-ω-amino acid-$^{Boc}$PNA-OH.

Since Fmoc-ω-amino acid-$^{Boc}$PNA-OH functions as a precursor of the PNA monomer unit, it can be referred to as a precursor PNA monomer unit.

Although an integer of 1 to 15 may be suitably selected for n in formula (I), a larger value of n is preferable with respect to diminishing the steric repulsion (or hindrance) during hybrid formation.

Next, as indicated below, oligomer Ia is synthesized using the precursor PNA monomer unit.

More specifically, a PNA monomer unit having adenine, guanine, cytosine or thymine protected with such as an N-benzyloxycarbonyl group is reacted with the precursor PNA monomer unit, and the PNA chain is sequentially condensed and elongated using a solid phase carrier for the tBoc method.

Although it is necessary to eliminate the tBoc group in advance to condense the PNA chain, there are no restrictions on the method used to accomplish this, and ordinary methods are used. For the subsequent condensation, a typical condensing agent such as HATU, HBTU or BOP is used.

In addition, although there are no particular restrictions on the solid carrier provided it can be used for tBoc, MBHA is used particularly preferably.

Next, as indicated below, the Fmoc group is selectively deprotected by piperidine treatment to convert to an amino group and obtain Ib.

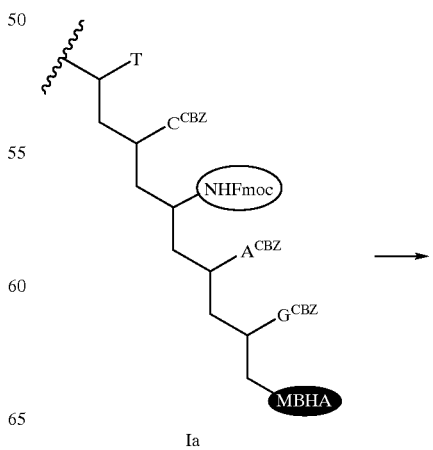

Ia

-continued

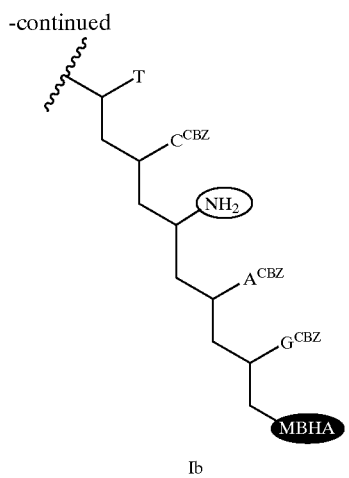

Ib

Moreover, as indicated below, a functional molecule having a free carboxylic acid group for the above amino group of the Ib is dehydrated and condensed to obtain Ic.

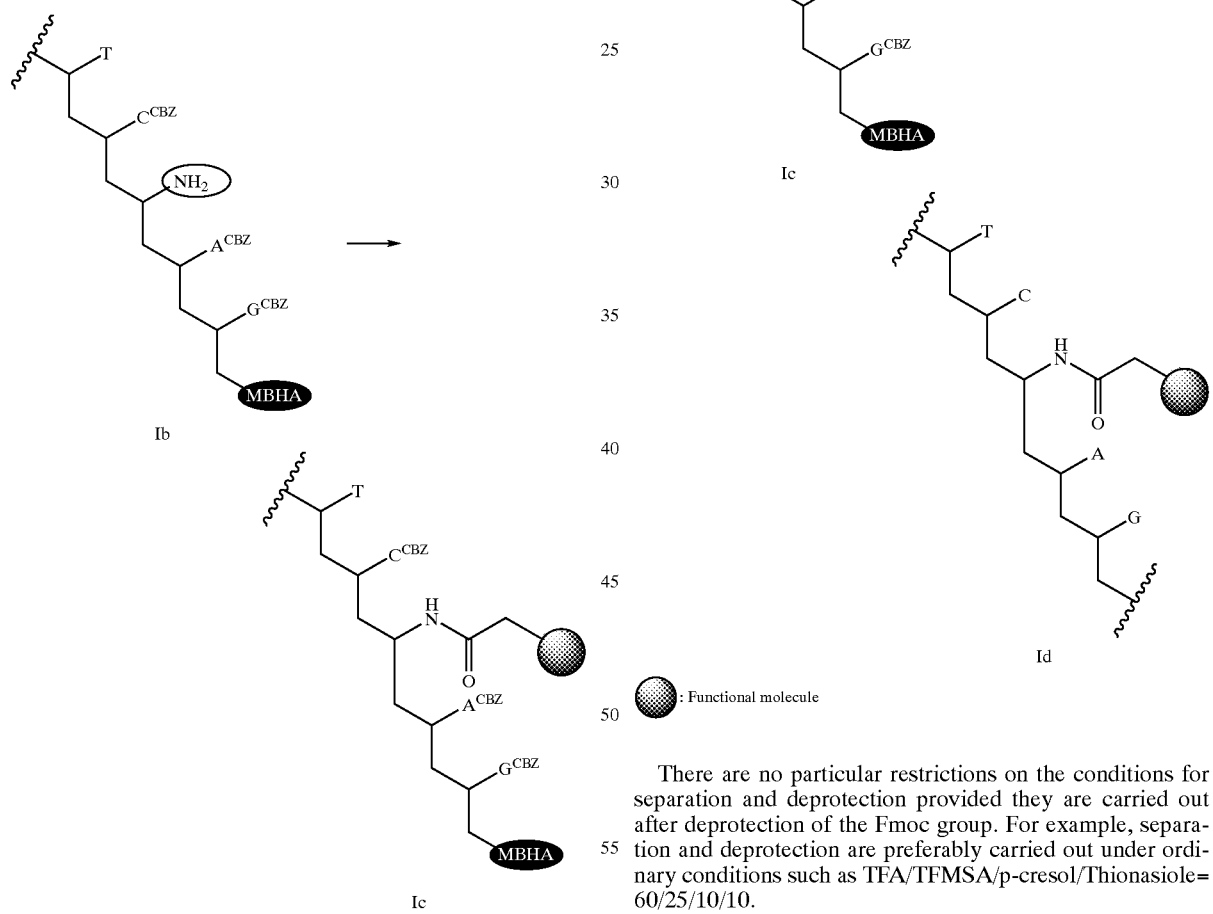

Ib

Ic

Although there are no particular restrictions on the above carboxylic acid group, an aliphatic carboxylic acid group is superior to an aromatic carboxylic acid group in terms of reactivity. Thus, the use of an aliphatic carboxylic acid group is preferable in terms of higher production efficiency.

In addition, deprotection of the Fmoc group by piperidine treatment is carried out preferably by taking a certain amount of time. The duration of this treatment is particularly preferably 20 to 40 minutes, and most preferably 30 minutes There are no particular restrictions on the condensing agent, and similar to the previously mentioned condensation of the PNA chain, a typical condensing agent such as HATU, HBTU or BOP is used.

It should be noted that introduction of functional molecules may be carried out immediately after condensation of Fmoc-ω-amino acid-$^{Boc}$PNA-OH (Method 1), or carried out after sequentially condensing all PNA monomer units including Fmoc-ω-amino acid-$^{Boc}$PNA-OH (Method 2).

Finally, as indicated below, the target PAN oligomer Id is obtained by simultaneously carrying out separation from the carrier resin and deprotection of the Z groups.

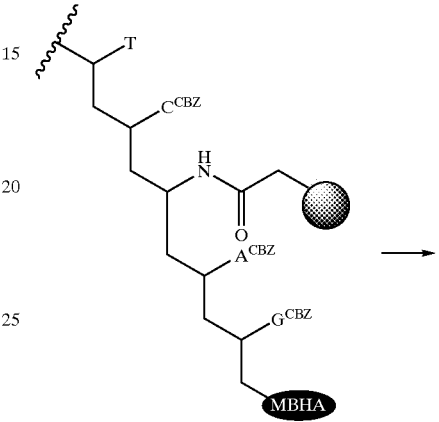

Ic

Id

: Functional molecule

There are no particular restrictions on the conditions for separation and deprotection provided they are carried out after deprotection of the Fmoc group. For example, separation and deprotection are preferably carried out under ordinary conditions such as TFA/TFMSA/p-cresol/Thionasiole= 60/25/10/10.

As has been described above, in the method according to the present invention, differing from methods requiring synthesis of an active ester used to synthesize functional monomers of the prior art, functional molecules can be used directly. In addition, various functional molecules can be introduced once Ia has been synthesized thereby enabling rapid and parallel synthesis of various types of PNA probes, which was difficult in the prior art.

According to the method of the present invention that includes a reaction between Fmoc-ω-amino acid-$^{Boc}$PNA- OH and a molecule having a PNA chain, compounds such as that indicated by the following general formula (II) are preferably synthesized:

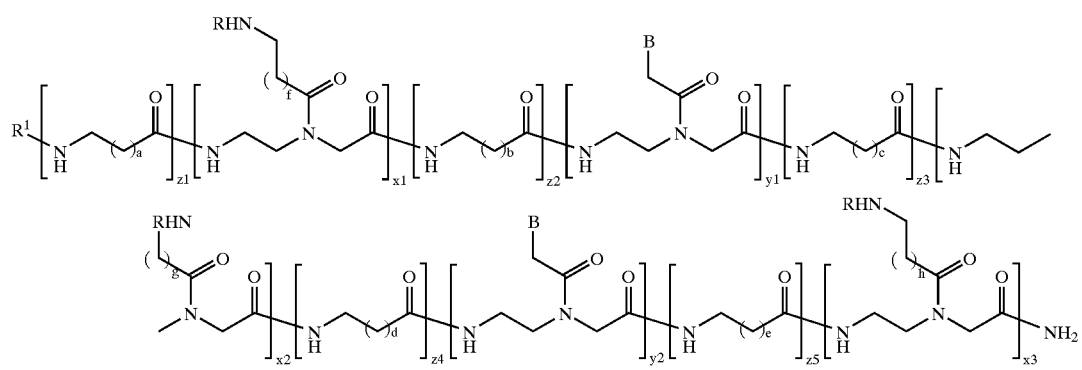

(II)

(wherein B's each independently are the same or different and represent adenine, guanine, cytosine or thymine, R's each independently are the same or different and represent an Fmoc group or a functional carboxylic acid derivative, $R^1$ represents a hydrogen atom or a functional carboxylic acid derivative, a through h represent integers of 0–10, $X_1$ through $X_3$, $Y_1$, $Y_2$ and $Z_1$ through $Z_5$ all represent integers of 0 or more, $X_1+X_2+X_3 \geq 0$, $Y_1+Y_2>0$, and $Z_1+Z_2+Z_3+Z_4+Z_5 \geq 0$, provided that $X_1+X_2+X_3$ and $Z_1+Z_2+Z_3+Z_4+Z_5$ are not simultaneously 0, and in the case where $X_1+X_2+X_3=0$, $R^1$ is a functional carboxylic acid derivative).

According to the method of the present invention, as compounds represented by formula (II), compounds in which R contains a carboxylic acid derivative of methyl red, $X_1+X_2+X_3=9$, $Y_1+Y_2=1$, $Y_1=3$ and $X_2=6$, or $Y_1=1$ and so forth are synthesized particularly preferably.

In addition, in the compounds represented by the above-mentioned general formula (II), compounds in which R or $R^1$ are cell membrane-permeable functional molecules are preferably synthesized as examples of compounds in which a plurality of functional molecules are introduced. Such compounds are typically compounds in which R represents a derivative of a cell membrane-permeable functional molecule and so forth, while $R^1$ represents a functional carboxylic acid derivative of a photofunctional molecule and so forth, namely compounds in which functional molecules are introduced at a plurality of sites containing terminal sections, and a plurality of functions are imparted by those functional molecules. Such compounds can be schematically represented in the manner indicated below.

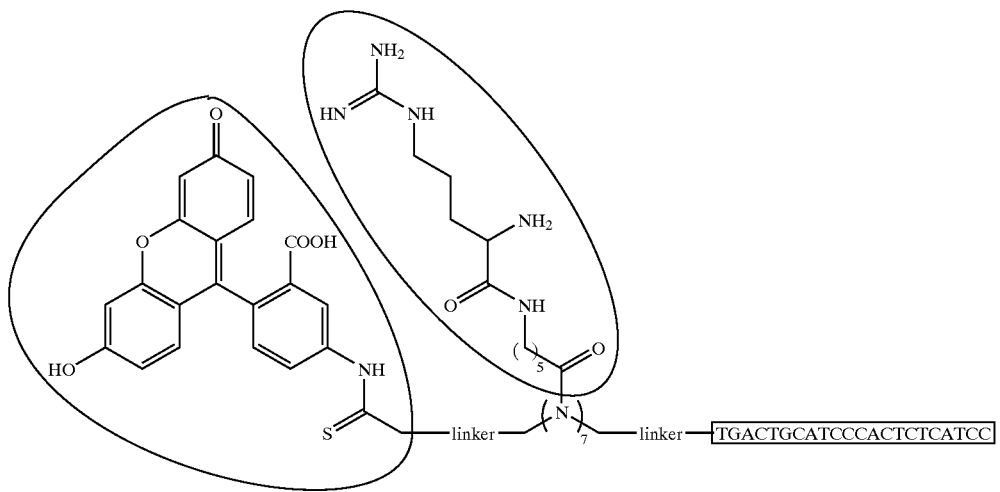

Such compounds are compounds in which $X_1=Z_1=Z_2=1$ and $Y_1 \geq 2$ in the above-mentioned general formula (II). Such compounds are preferable in terms of ease of synthesis, cost of synthesis and so forth..

Although there are no particular restrictions on the above compounds provided a, b and f each are an integer of 0 to 10, even in the case of compounds in which, for example, a $\leq 6$, b$\leq 4$ and f$\leq 6$, there are no problems in terms of either synthesis or practical use.

The introduction of linker sites makes it possible to prevent interference by individual functional sites and base sequence recognition sites while also enhancing the reliability of molecule function. The terms PNA, PNA monomer and PNA oligomer in the present specification include those that contain linker sites at their terminals and/or inside.

In addition to the above linker sites, f through h in general formula (I) can also be selected as desired to serve as sites for preventing mutual interference between these sites or regions.

Examples of groups that compose linker sites include linear or branched hydrocarbons and their ether forms. Linear hydrocarbon groups are preferable in terms of ease of introduction and cost, and linear hydrocarbon groups having 1 to 6 carbon atoms are particularly preferable. In addition, ether forms are preferable in terms of their universality.

Compounds in which the above plurality of functional molecules have been introduced are preferably synthesized using, for example, Koch, T., Hansen, H. F., Andersen, P., Larsen, T., Batz, H. G., Otteson, K. and Orum, H.: *Peptide Res* 1997, 49, 80–88.

Base sequence recognition sites can be converted to oligomers by solid phase synthesis using various commercially available PNA monomers. Commercially available Boc-7-aminoheptanoic acid or Boc-6-aminocaproic acid and so forth can he used for linker sites.

Introduction of a photofunctional molecule as a single functional molecule enables fluorescent labeling, and compounds can be synthesized that have other functions as well. Although various fluorescent emission wavelengths can be selected using commercially available active ester-type fluorescent labeling compounds such as FITC, ROX, TAMRA and Dabcyl for use as fluorescent labeling sites, fluorescent labeling compounds that are introduced are not limited to these.

Examples of other functions capable of being introduced into compounds of the present invention include membrane permeation function. These membrane permeation function sites can be similarly introduced by using a compound represented by the aforementioned general formula (I). Examples of functional molecules capable of improving membrane permeability include arginine, but lysine, serine and other water-soluble amino acids can also be used preferably.

In addition, it is also possible to introduce a plurality of amino acids by utilizing the Fmoc amino acid unit. Examples of this synthesis are shown in Examples 20 and 21. However, the above two compounds are merely model compounds of a fluorescent PNA probe having membrane permeation function, and the present invention is not limited by these.

These probes are characterized by being entirely of the PNA type and being completely resistant to enzymes. Namely, previous probes having a membrane permeation function consisted primarily of those comprised by covalent bonding of PNA and a peptide chain or phospholipid having membrane permeation function. Although these probes have superior membrane permeation function, once they enter inside a cell, the peptide chain or phospholipid is predicted to be decomposed by enzymes. Thus, these have the disadvantage that a probe having been subjected to decomposition as a result of not recognizing the target cannot be completely removed in the washing step.

In contrast, since the probe designed here is not subjected to decomposition by enzymes even within cells, a probe that has not recognized the target can be completely removed in the washing step, thereby enabling an accurate determination of the amount of gene expressed.

It should be noted that in addition to compounds having these functional characteristics, organ-selective functional molecules such as lactose and Tris-X, bactericidal functional molecules such as tanatin and cecropin, as well as molecule-recognizing functional molecules such as viologen can also be introduced according to the present invention without limitation, and such compounds can be used practically in large volumes and at low cost.

EXAMPLE

The invention will be illustrated in more detail by way of examples, but the invention is not limited to these examples.

Example 1

Synthesis of Fmoc-Gly-$^{Boc}$PNA-OH (1)

To a solution of Fmoc-Gly-OH (891 mg, 3.0 mmol) and PfpOH(754 mg, 4.5 mmol) in DMF (12 mL) was added DCC (845 mg, 4.5 mmol) at 0° C. for 30 min and then room temperature for 15 h. The reaction mixture was filterd to remove DCUrea and the flitrate was evaporated in vacuo to give the crude Fmoc-Gly-OPfp. To a solution of Fmoc-Gly-OPfp and $^{Boc}$PNA-OH (436 mg, 2.0 mmol) in DMF (16 mL) was added diisoprppylethylamine (445 il, 2.6 mmol) and the reaction mixture was stirred at room temperature for 15 h. The reaction mixture was evaporated in vacuo and the residue was flush-chromatographed (0–50% MeOH/$CH_2Cl_2$) to give Fmoc-Gly-$^{Boc}$PNA-OH (121 mg, 12%). $^1$H NMR (DMSO-$d_6$) δ 7.88 (d, J=7.0 Hz, 2H), 7.72 (d, J=7.0 Hz, 2H), 7.62 (brt) and 7.56 (brt) (1H), 7.41 (t, J=7.0 Hz, 2H), 7.33 (t, J=7.0 Hz, 2H), 7.18 (m, 2H), 6.85 (brt) and 6.79 (brt) (1H), 4.35–4.15 (m, 3H), 4.05–3.85 (m, 3H), 3.77 (m, 1H), 3.40–3.25 (m, 2H), 3.10 (m) and 3.03 (s) (2H), 1.37 (brs, 9H); $^{13}$C NMR (DMSO-$d_6$) δ 172.2 (d), 169.10 (d), 156.34 (d), 155.58 (d), 143.83, 140.66, 127.58, 127.04, 125.24, 120.04, 77.77 (d), 65.71, 47.34 (d), 46.72, 46.65 (d), 29.23 (d), 28.14 (d); FABMS m/z 498 [(M+H)$^+$].

Example 2

Synthesis of Fmoc-$C_7$-OPfp

DCC (381.9 mg, 1.0 mmol) was added with ice cooling to a DMF (2.5 mL) solution of Fmoc-$C_7$—OH (381.9 mg, 1.0 mmol) and PfpOH (349.7 mg, 1.9 mmol), and the reaction mixture was stirred for 30 min at 0° C. and then overnight at room temperature. The reaction mixture was filtered to remove DCUrea, the filtrate was concentrated under reduced pressure, and the residue was purified by silica gel column chromatography ($CH_2Cl_2$). After concentration, the residue was recrystallized from hexanes to give Fmoc-$C_7$-OPfp as a white powder (537.5 mg, 98%). $^1$H-NMR(CDCl$_3$) δ 7.76 (d, J=7.6 Hz, 2H), 7.59 (d, J=7.6 Hz, 2H), 7.40 (t, J=7.4 Hz, 2H), 7.31 (t, J=7.4 Hz, 2H), 4.70–4.73 (brt, 1H), 4.47–4.40 (brd, 2H), 4.22 (t, J=6.42 Hz, 1H), 3.20 (q, J=5.94 Hz, 2H), 2.66 (t, J=7.38 Hz, 2H), 1.80–1.75 (m, 2H), 1.55–1.50 (m, 2H), 1.45–1.34 (m, 6H) ; $^{13}$C-NMR (CDCl$_3$) δ 169.44, 156.43, 143.98, 141.96 (m), 141.29, 140.23, 138.67 (m), 136.99 (m), 127.60, 126.96, 124.97, 119.91, 66.49, 55.73, 47.29, 41.34 (d), 34.89, 33.22, 29.85, 28.70, 26.42, 25.43, 24.60; HRMS (FAB$^+$) calcd for $C_{29}H_{27}F_5NO_4$ [(M+H)$^+$] 547.5131, observed 548.1861.

Example 3

Synthesis of Fmoc-Gly-$^{Boc}$PNA-OH (2)

To a solution of NaHCO$_3$ (67.2 mg, 0.8 mmol), H$_2$O (1.0 mL), and acetone (6.0 mL) was added Fmoc-Gly-OPfp (240.9 mg, 0.52 mmol) and $^{Boc}$PNA-OH (87.3 mg, 0.4 mmol) and the reaction mixture was stirred at room temperature for 4 h. The reaction mixture was cooled down at 0° C. and adjusted at pH 3.0 using chilled 1 N aqueous HCl. The solution, to which 1% aqueous citric acid was added, was extracted with EtOAc and the combined organic layers was washed with brine, dired over MgSO$_4$ and evaporated in vacuo. The residue was flush-chromatographed (1–5%

MeOH/CH$_2$Cl$_2$) to give the crude Fmoc-Gly-$^{Boc}$PNA-OH (157.3 mg, 80%) as an amorphous white powder.

Example 4

Synthesis of Fmoc-β-Ala-$^{Boc}$PNA-OH (1)

To a solution of Fmoc-β-Ala-OH (311 mg, 1.0 mmol) and PfpOH(334 mg, 1.75 mmol) in DMF (2.5 mL) was added DCC (288 mg, 1.4 mmol) at 0° C. for 30 min and then room temperature for 15 h. The reaction mixture was filterd to remove DCUrea, the flitrate was evaporated in vacuo, and the residue was flush-chromatographed (CH$_2$Cl$_2$). The crude Fmoc-β-Ala-OPfp was recrystallized using hexane and CH$_2$Cl$_2$ to give the pure Fmoc-β-Ala-OPfp (429 mg 90%) as a white powder. To a solution of Fmoc-β-Ala-OPfp (100 mg, 0.21 mmol) and $^{Boc}$PNA-OH (41 mg, 0.19 mmol) in DMF (2 mL) was added diisoprppylethylamine (36 il, 0.21 mmol) and the reaction mixture was stirred at room temperature for 15 h. The reaction mixture was evaporated in vacuo and the residue was flush-chromatographed (0–10% MeOH/CH$_2$Cl$_2$) to give Fmoc-Gly-$^{Boc}$PNA-OH (41 mg, 42%). $^1$H NMR (DMSO-d$_6$) δ 7.88 (d, J=7.4 Hz, 2H), 7.68 (d, J=7.4 Hz, 2H), 7.41 (t, J=7.3 Hz, 2H), 7.33 (t, J=7.3 Hz, 2H), 7.18 (m, 2H), 6.83 (brt) and 6.72 (brt) (2H), 4.3–4.2 (m, 4H), 4.05–3.9 (m, 3H), 3.33 (brt) and 3.29 (brt) (2H), 3.19 (m, 2H), 3.07 (brq) and 3.02 (brq) (2H), 1.36 (brs, 9H) ; $^{13}$C NMR (DMSO-d$_6$) δ 171.20 (d), 170.85 (d), 155.93, 155.56, 143.87, 140.69, 127.55, 127.01, 125.09, 120.05, 77.73 (d), 65.30 (d), 59.69, 47.35 (d), 46.68, 46.49 (d), 37.99 (d), 36.72 (d), 28.14 (d).

Example 5

Synthesis of Fmoc-β-Ala-$^{Boc}$PNA-OH (2)

To a solution of NaHCO$_3$ (92.4 mg, 1.1 mmol), H$_2$O (1.25 mL), and acetone (1.25 mL) was added Fmoc-β-Ala-OPfp (476.0 mg, 1.0 mmol) and $^{Boc}$PNA-OH (87.3 mg, 0.55 mmol) and the reaction mixture was stirred at room temperature for 6 h. The reaction mixture was cooled down at 0° C. and adjusted at pH 3.0 using chilled 1 N aqueous HCl. The solution, to which 1% aqueous citric acid was added, was extracted with EtOAc and the combined organic layers was washed with brine, dired over MgSO$_4$ and evaporated in vacuo. The residue was flush-chromatographed (1–5% MeOH/CH$_2$Cl$_2$) to give the crude Fmoc-β-Ala-$^{Boc}$PNA-OH (157.3 mg, 80%) as an amorphous white powder.

Example 6

Synthesis of Fmoc-GABA-$^{Boc}$PNA-OH (1)

To a solution of Fmoc-GABA-OPfp (100 mg, 0.20 mmol) and $^{Boc}$PNA-OH (40 mg, 0.18 mmol) in DMF (2 mL) was added diisoprppylethylamine (34 il, 0.20 mmol) and the reaction mixture was stirred at room temperature for 15 h. The reaction mixture was evaporated in vacuo and the residue was flush-chromatographed (0–20% MeOH/CH$_2$Cl$_2$) to give Fmoc-GABA-$^{Boc}$PNA-OH (43 mg, 45%). $^1$H NMR (DMSO-d$_6$) δ 7.88 (d, J=7.4 Hz, 2H), 7.68 (d, J=7.4 Hz, 2H),7.41 (t, J=7.4 Hz, 2H), 7.33 (t, J=7.4 Hz, 2H), 7.29 (m, 1H), 6.82 (brt) and 6.71 (brt) (1H), 4.3–4.2 (m, 4H), 4.05–3.9 (m, 3H), 3.35–3.25 (m, 2H), 3.1–2.95 (m, 4H), 1.36 (brs, 9H); $^{13}$C NMR (DMSO-d$_6$) δ 172.2 (d), 171.5 (d), 156.03, 155.60 (d), 143.89, 140.68, 127.54, 127.00, 125.50, 120.04, 77.70 (d), 65.19, 54.84, 46.97 (d), 46.72, 38.20 (d), 29.23 (d), 28.14 (d), 24.98 (d).

Example 7

Synthesis of Fmoc-GABA-OPfp

DCC (248 mg, 1.2 mmol) was added with ice cooling to a DMF (2.5 mL) solution of Fmoc-GABA-OH (325 mg, 1.0 mmol) and PfpOH (221 mg, 1.2 mmol), and the reaction mixture was stirred for 30 min at 0° C. and then for 15 h at room temperature. The reaction mixture was filtered, the filtrate was concentrated under reduced pressure, and the residue was purified by, silica gel column chromatography (CH$_2$Cl$_2$). After concentration, the residue was recrystallized from hexanes to give Fmoc-GABA-OPfp as a white powder (463 mg, 94%). $^1$H NMR (CDCl$_3$) δ 7.77 (d, J=7.5 Hz, 2H), 7.59 (d, J=7.5 Hz, 2H), 7.40 (t, J=7.5 Hz, 2H), 7.31 (t, J=7.5 Hz, 2H), 4.85 (brs, 1H), 4.45 (d, J=6.3 Hz, 2H), 4.21 (t, J=6.3 Hz, 2H), 3.32 (d, J=6.5 Hz, 2H), 2.71 (t, J=6.5 Hz, 2H), 1.98 (t, J=6.5 Hz, 2H); $^{13}$C NMR (CDCl$_3$) δ 169.02, 156.49, 143.83, 141.87 (m), 141.28, 140.23 (m), 138.61 (m), 136.94 (m), 127.62, 127.46, 124.89, 119.88, 66.52, 47.25, 39.92, 30.42, 25.03.

Example 8

Synthesis of Fmoc-GABA-$^{Boc}$PNA-OH (2)

To a solution of NaHCO$_3$ (67.2 mg, 0.8 mmol), H$_2$O (1.0 mL), and acetone (5.0 mL) was added Fmoc-GABA-OPfp (255.5 mg, 0.52 mmol) and $^{Boc}$PNA-OH (87.3 mg, 0.4 mmol) and the reaction mixture was stirred at room temperature for 8 h. The reaction mixture was cooled down at 0° C. and adjusted at pH 3.0 using chilled 1 N aqueous HCl. The solution, to which 1% aqueous citric acid was added, was extracted with EtOAc and the combined organic layers was washed with brine, dired over MgSO$_4$ and evaporated in vacuo. The residue was flush-chromatographed (1–5% MeOH/CH$_2$Cl$_2$) to give the crude Fmoc-GABA-$^{Boc}$PNA-OH (175.9 mg, 84%) as an amorphous powder.

Example 9

Synthesis of Fmoc-C$_4$-$^{Boc}$PNA-OH

To a solution of NaHCO$_3$ (67.2 mg, 0.8 mmol), H$_2$O (1.0 mL), and acetone (4.0 mL) was added Fmoc-C$_4$-OPfp (323.5 mg, 0.64 mmol) and $^{Boc}$PNA-OH (87.3 mg, 0.4 mmol) and the reaction mixture was stirred at room temperature for 12 h. The reaction mixture was cooled down at 0° C. and adjusted at pH 3.0 using chilled 1 N aqueous HCl. The solution, to which 1% aqueous citric acid was added, was extracted with EtOAc and the combined organic layers was washed with brine, dired over MgSO$_4$ and evaporated in vacuo. The residue was flush-chromatographed (1–5% MeOH/CH$_2$Cl$_2$) to give the crude Fmoc-C$_4$-$^{Boc}$PNA-OH (190.7 mg, 88%) as an amorphous powder. $^1$H-NMR (CDCl$_3$) δ 7.76 (d, J=6.7, 2H), 6.96 (mi) and 6.66 (ma) (brd, J=6.7 Hz, 2H), 7.41–7.37 (m, 2H), 7.32–7.28 (m, 2H), 7.14 (ma) and 6.68 (mi) (m, 1H), 5.54 (ma) and 5.43 (mi) (brt, 1H), 4.45 (mi) and 4.37 (ma) (m, 2H), 4.24–4.21 (m, 1H), 4.08–3.95 (m, 2H), 3.54–3.48 (m, 2H), 3.29–3.11 (m, 4H), 2.43–2.25 (m, 2H), 1.70–1.29 (m, 13H); $^{13}$C-NMR (CDCl$_3$) δ 174.39, 173.07, 171.95, 157.51, 156.79 (d), 156.11, 144.06 (d), 141.16, 127.46 (d), 126.90 (d), 119.77 (d), 81.42, 79.67, 66.39 (d), 53.35, 49.46 (d), 49.17, 48.60, 47.15 (d), 40.89, 40.32 (d), 38.68, 31.87, 31.41, 29.59, 29.11 (d), 28.28, 21.77 (d); HRMS(FAB$^+$) calcd for C$_{29}$H$_{37}$N$_3$O$_7$ [(M+H)$^+$] 539.2632, observed 540.2707.

Example 10

Synthesis of Fmoc-C$_5$-$^{Boc}$PNA-OH

To a solution of NaHCO$_3$ (67.2 mg, 0.8 mmol), H$_2$O (1.0 mL), and acetone (7.5 mL) was added Fmoc-C$_5$-OPfp (311.0 mg, 0.6 mmol) and $^{Boc}$PNA-OH (87.3 mg, 0.4 mmol) and the reaction mixture was stirred at room temperature for 24 h. The reaction mixture was cooled down at 0° C. and adjusted at pH 3.0 using chilled 1 N aqueous HCl. The solution, to which 1% aqueous citric acid was added, was extracted with EtOAc and the combined organic layers was washed with brine, dired over MgSO$_4$ and evaporated in vacuo. The residue was flush-chromatographed (1–5% MeOH/CH$_2$Cl$_2$) to give the crude Fmoc-C$_5$-$^{Boc}$PNA-OH (198.0 mg, 90%) as a white amorphous powder. $^1$H-NMR (DMSO-d$_6$) δ 7.88 (d, J=7.4 Hz, 2H), 7.68 (d, J=7.2 Hz, 2H), 7.41 (t, J=7.4 Hz, 2H), 7.32 (t, J=7.4 Hz, 2H), 7.22 (brt, 1H), 6.81 (ma) and 6.67 (mi) (brt, 1H), 4.33 (mi) and 4.29 (ma) (brd, 2H), 4.20 (t, J=7.1 Hz, 1H), 4.08 (mi) and 3.90 (ma) (brs, 2H), 3.09–2.94 (m, 4H), 2.30 (ma) and 2.14 (mi) (brt, 2H), 1.51–1.45 (m, 2H), 1.41–1.31 (brs, 11H), 1.29–1.21 (m, 8H); $^{13}$C-NMR (CDCl$_3$) δ 175.1 (d), 172.27 (d), 157.20 (t), 156.63, 144.43 (d), 141.69, 128.07, 127.45, 125.40 (d), 120.35, 81.71, 80.00, 67.36 (d), 50.42, 49.81 (d), 48.90 (d), 47.82 (d), 41.77, 41.16, 40.64, 39.19, 33.12, 32.75, 29.45 (d), 28.81, 26.59, 24.97, 24.70; HRMS (FAB$^+$) calcd for C$_{30}$H$_{39}$N$_3$O$_7$ [(M+H)$^+$] 553.2788, observed 554.2873.

Example 11

Synthesis of Fmoc-C$_6$-$^{Boc}$PNA-OH

To a solution of NaHCO$_3$ (67.2 mg, 0.8 mmol), H$_2$O (1.0 mL), and acetone (6.0 mL) was added Fmoc-C$_6$-OPfp (331.9 mg, 0.6 mmol) and $^{Boc}$PNA-OH (87.3 mg, 0.4 mmol) and the reaction mixture was stirred at room temperature for 24 h. The reaction mixture was cooled down at 0° C. and adjusted at pH 3.0 using chilled 1 N aqueous HCl. The solution, to which 1% aqueous citric acid was added, was extracted with EtOAc and the combined organic layers was washed with brine, dired over MgSO$_4$ and evaporated in vacuo. The residue was flush-chromatographed (1–5% MeOH/CH$_2$Cl$_2$) to give the crude Fmoc-C$_6$-$^{Boc}$PNA-OH (197.0 mg, 87%) as an amorphous white powder. $^1$H-NMR (DMSO-d$_6$) δ 7.88 (d, J=7.7 Hz, 2H), 7.68 (ma) and 7.63 (mi) (brd, J=7.4 Hz, 2H), 7.40 (t, J=7.4 Hz, 2H), 7.32 (t, J=7.4 Hz, 2H), 7.22 (brt, 1H), 6.79 (ma) and 6.66 (mi)(brt, 1H), 4.39 (mi) and 4.29 (ma) (brd, 2H), 4.20 (brt, J=6.7 Hz, 1H), 4.08 (mi) and 3.91 (ma) (brs, 2H), 3.10–2.97 (m, 4H), 2.31 (ma) and 2.15 (mi) (brt, 2H), 1.50–1.47 (m, 2H), 1.41–1.36 (m, 11H), 1.28–1.24 (brd, 6H) ; $^{13}$C-NMR (CDCl$_3$) δ 175.23 (d), 172.41 (d), 157.11 (d), 156.60, 144.34 (d), 141.69, 128.07, 127.45, 125.40 (d), 120.35, 81.68, 80.00 (d), 67.72, 67.50 (d), 53.87, 50.77, 50.14 (d), 48.90, 47.82 (d), 41.29 (d), 41.36, 40.69, 39.18, 33.19, 32.96, 30.00, 29.11, 28.81, 26.75 (d), 25.27 (d), 24.80 (d); HRMS (FAB$^+$) calcd for C$_{29}$H$_{41}$N$_3$O$_7$ [(M+H)$^+$] 567.2945, observed 568.3027.

Example 12

Synthesis of Fmoc-C$_7$-$^{Boc}$PNA-OH

To a solution of NaHCO$_3$ (67.2 mg, 0.8 mmol), H$_2$O (1.0 mL), and acetone (7.0 mL) was added Fmoc-C$_7$-OPfp (328.5 mg, 0.6 mmol) and $^{Boc}$PNA-OH (87.3 mg, 0.4 mmol) and the reaction mixture was stirred at room temperature for 24 h. The reaction mixture was cooled down at 0° C. and adjusted at pH 3.0 using chilled 1 N aqueous HCl. The solution, to which 1% aqueous citric acid was added, was extracted with EtOAc and the combined organic layers was washed with brine, dired over MgSO$_4$ and evaporated in vacuo. The residue was flush-chromatographed (1–5% MeOH/CH$_2$Cl$_2$) to give the crude Fmoc-C$_7$-$^{Boc}$PNA-OH (196.1 mg, 84%) as an amorphous white powder. $^1$H-NMR (DMSO-d6) δ 7.88 (d, J=7.7 Hz, 2H), 7.68 (ma) and 7.63 (mi) (brd, J=7.4 Hz, 2H), 7.40 (t, J=7.4 Hz, 2H), 7.32 (t, J=7.4 Hz, 2H), 7.22 (brt, 1H), 6.79 (ma) and 6.79 (mi) (brt, 1H), 4.39 (mi) and 4.29 (ma) (brd, J=6.9 Hz, 2H), 4.05 (t, J=6.7 Hz, 1H), 4.08 (mi) and 3.91 (ma) (brs, 2H), 3.12–2.95. (m, 4H), 2.31 (mi) and 2.15 (ma) (brt, 2H), 1.50–1.47 (m, 2H), 1.42–1.34 (m, 11H), 1.25 (brd, 2H) ; $^{13}$C-NMR (CDCl$_3$) δ 174.72, 172.19, 156.52, 156.05, 143.78 (d), 141.14, 127.51, 126.89, 124.86 (d), 119.79, 79.43 (d), 66.80 (d), 53.33, 50.19, 49.20, 48.50, 47.14 (d), 41.18 (d), 38.60, 32.28 (d), 29.60, 28.83, 28.26, 26.27 (d), 24.68 (d), 21.77 (d) ; HRMS (FAB$^+$) calcd for C$_{32}$H$_{43}$N$_3$O$_7$ [(M+H)$^+$] 581.3101, observed 582.3171.

Example 13

Synthesis of Fmoc-C$_{10}$-$^{Boc}$PNA-OH

To a solution of NaHCO$_3$ (67.2 mg, 0.8 mmol), H$_2$O (1.0 mL), and acetone (7.0 mL) was added Fmoc-C$_{10}$-OPfp (353.7 mg, 0.6 mmol) and $^{Boc}$PNA-OH (87.3 mg, 0.4 mmol) and the reaction mixture was stirred at room temperature for 24 h. The reaction mixture was cooled down at 0° C. and adjusted at pH 3.0 using chilled 1 N aqueous HCl. The solution, to which 1% aqueous citric acid was added, was extracted with EtOAc and the combined organic layers was washed with brine, dired over MgSo$_4$ and evaporated in vaclio. The residue was flush-chromatographed (1–5% MeOH/CH$_2$Cl$_2$) to give the crude Fmoc-C$_{10}$-$^{Boc}$PNA-OH (218.5 mg, 88%) as an amorphous white powder. $^1$H-NMR (CDCl$_3$) δ 9.60 (brs, 1H), 7.73 (d, J=7.6 Hz, 2H), 7.58 (d, J=6.8 Hz, 2H), 7.37 (t, J=6.8 Hz, 2H), 7.29 (t, J=7.2 Hz, 2H), 5.52 (ma) and 5.35 (mi) (brd, 1H), 5.00 (s, 1H), 4.45 (mi) and 4.40 (ma) (brd, J=6.4 Hz, 2H), 4.23–4.22 (m, 1H), 4.09 (mi) and 4.04 (ma) (brs, 2H), 3.57–3.46 (m, 2H), 3.29–3.03 (m, 4H), 1.66–1.58 (brs, 2H), 1.52–1.37 (m, 11H), 1.33–1.20 (brs, 12H); $^{13}$C-NMR (CDCl$_3$) δ 174.5 (d), 172.43 (d), 171.64 (d), 157.83 (d), 156.98, 156.03, 143.78 (d), 141.17, 127.52, 126.90, 124.86 (d), 119.70 (d), 81.08, 79.43 (d), 67.26, 66.43, 50.14, 49.29, 48.15 (d), 47.17 (t), 41.47, 40.99, 40.16, 38.63, 32.90, 32.43 (d), 29.55 (d), 29.22 (m), 28.28, 26.56 (d), 24.98, 24.75; HRMS (FAB$^+$) calcd for C$_{35}$H$_{49}$N$_3$O$_7$ [(M+H)$^+$] 623.3571, observed 624.3643.

Example 14

Synthesis of Fmoc-C$_{11}$-OPfp

DCC (309.5 mg, 3.0 mmol) was added with ice cooling to a DMF (2.5 mL) solution of Fmoc-C$_{11}$—OH (437.5 mg, 2.0 mmol) and PfpOH (276.6 mg, 3.0 mmol), and the reaction mixture was stirred for 30 min at 0° C. and then for 18 h at room temperature. The reaction mixture was filtered to remove DCUrea, the filtrate was concentrated under reduced pressure, and the residue was purified by silica gel column chromatography (CH$_2$Cl$_2$). After concentration, the residue was recrystallized from hexanes to give Fmoc-C$_{11}$-OPfp as a white powder (575.6 mg, 96%). $^1$H NMR (CDCl$_3$) δ 7.79 (d, J=7.6 Hz, 2H), 7.63 (d, J=7.2 Hz, 2H), 7,43 (t, J=7.6 Hz, 2H), 7.34 (t, J=7.2 Hz, 2H), 4.86 (brt, 1H), 4.47 (mi) and 4.44 (ma) (brd, 2H), 4.25 (t, 1H), 3.22 (q, J=6.1 Hz, 2H), 2.68 (t, J=7.2 Hz, 2H), 1.80 (m, 2H), 1.56–1.52 (m, 2H), 1.47–1.42 (m, 2H), 1.39–1.30 (m, 12H); HRMS (FAB$^+$) calcd for $C_{33}H_{34}F_5NO_4$ [(M+H)$^+$] 603.6194, observed 604.2490.

Example 15

Synthesis of Fmoc-$C_{11}$-$^{Boc}$PNA-OH

To a solution of NaHCO$_3$ (67.2 mg, 0.8 mmol), H$_2$O (1.0 mL), and acetone (10 mL) was added Fmoc-C$_{11}$-OPfp (362.2 mg, 0.6 mmol) and $^{Boc}$PNA-OH (87.3 mg, 0.4 mmol) and the reaction mixture was stirred at room temperature for 48 h. The reaction mixture was cooled down at 0° C. and adjusted at pH 3.0 using chilled 1 N aqueous HCl. The solution, to which 1% aqueous citric acid was added, was extracted with EtOAc and the combined organic layers was washed with brine, dired over MgSO$_4$ and evaporated in vacuo. The residue was flush-chromatographed (1–5% MeOH/CH$_2$Cl$_2$) to give the crude Fmoc-C$_{11}$-$^{Boc}$PNA-OH (227.6 mg, 89%) as an amorphous white powder. $^1$H-NMR (CDCl$_3$) δ 9.62 (brs, 1H), 7.74 (d, J=7.6 Hz, 2H), 7.57 (d, J=7.5 Hz, 2H), 7.37 (t, J=7.1 Hz, 2H), 7.28 (t, J=6.8 Hz, 2H), 5.53 (ma) and 5.35 (mi) (brs, H), 5.00 (brt, 1H), 4.43 (mi) and 4.37 (ma) (brd, J=6.4 Hz, 2H), 4.22–4.19 (m, 1H), 4.06 (mi) and 4.01 (ma) (brs, 2H), 3.51–3.44 (m, 2H), 3.23–3.08 (m, 4H) 2.36 (ma) and 2.21 (mi) (brt, J=7.0 Hz, 2H), 1.69–1.58 (brs, 2H), 1.52–1.40 (m, 11H), 1.29–1.25 (brd, 14H); $^{13}$C-NMR (CDCl$_3$) δ 175.45 (d), 172.43 (d), 157.91 (d), 157.01, 156.57, 144.33 (d), 141.72, 128.05, 127.43, 125.40 (d), 120.35, 81.63, 80.00 (d), 67.77, 66.97, 50.67, 49.84, 49.20 (d), 47.72 (t), 42.10, 41.53, 40.70, 39.18, 33.51, 33.07, 30.03, 29.83 (m), 28.82, 27.00 (d), 25.44, 25.35; HRMS (FAB$^+$) calcd for $C_{36}H_{51}N_3O_7$ [(M+H)$^+$] 637.3727, observed 638.3794.

Example 16

Synthesis of PNA Oligomer 1 (H$_2$N-G-A-T-p MR-G-A-C-G-C—CONH$_2$) (Method 1)

Lowering titer of solid phase support Following the solid phase tBoc method previously reported by Koch et al. (Koch, T.; Hansen, H. F.; Andersen, P.; Larsen, T.; Batz, H. G.; Otteson, K.; Ørum, H. J. Peptide Res. 1997, 49, 80–88.), a condensation reaction was first carried out with MBHA solid phase support (50 mg) using cytosine PNA monomer unit (10.1 mg, 20 μmol), and HBTU (7.6 mg, 20 μmol) and DIEA (3.5 μL, 20 μmol) as the condensing agent, for 2 h at room temperature. Next, capping of unreacted amino groups was carried out three times using the capping reagent Ac$_2$O/pyridine/DMF (1/2/2) for 30 min at room temperature. Completion of the capping reaction was confirmed by ninhydrin reagent.

Design of a part of base sequence recognition (G-A-C-G-C) region After deprotecting the Boc group by a TFA treatment (95% TFA/5% m-cresol), a condensation reaction using guanine PNA monomer unit (7.7 mg, 20 μmol), and HBTU (7.6 mg, 20 μmol) and DIEA (3.5 μL, 20 μmol) as the condensing agent, was carried out on the MBHA for 30 min at room temperature. After confirming completion of the condensation reaction with ninhydrin reagent, capping of unreacted amino groups on the MBHA was carried out using the capping reagent Ac$_2$O/pyridine/DMF (1/25/25) for 5 min at room temperature. This process was repeated a further four times.

Design of photo-functional region The PNA precursor monomer unit Fmoc-Gly-$^{Boc}$PNA-OH (10.0 mg, 20 μmol) was condensed in succession using HBTU (7.6 mg, 20 μmol) and DIEA (3.5 μL, 20 μmol). Progress of the reaction was confirmed using ninhydrin reagent. After condensing the PNA precursor monomer unit, the Fmoc group was deprotected with a piperidine treatment (20% piperidine in DMF, room temperature, 3 min). The photoactive carboxylic acid derivative p-Methyl Red (10.8 mg, 40 μmol) was then condensed using HBTU (15.2 mg, 40 μmol) and DIEA (7.0 μL, 40 μmol) as the condensing agent, thereby incorporating the photoactive molecule into the target location.

Design of a rest part of base sequence recognition (G-A-T) region After deprotecting the Boc group by a TFA treatment (95% TFA/5% m-cresol), a condensation reaction using guanine PNA monomer unit (7.7 mg, 20 μmol), and HBTU (7.6 mg, 20 μmol) and DIEA (3.5 μL, 20 μmol) as the condensing agent, was carried out on the MBHA for 30 min at room temperature. After confirming completion of the condensation reaction with ninhydrin reagent, capping of unreacted amino groups on the MBHA was carried out using the capping reagent Ac$_2$O/pyridine/DMF (1/25/25) for 5 min at room temperature. This process was repeated a further two times.

Cleavage from support/purification Finally, cleavage from the solid phase support and deprotection of the Cbz group were carried out simultaneously using the cleavage reagent TFA/TFMSA/p-cresol/thioanisole (60/25/10/10). A gradient composed of A (0.05% TFA in water) and B (0.05% TFA in acetonitrile) was used for analytical and preparative HPLC: Time 0, 0% B. Time 50 min, 50% B (flow rate: 10 mL/min, detection: 260 nm). The purified PNA oligomer 1 was identified by MALDI-TOF MS. UV λmax (H$_2$O) 303, 548 (nm).

Example 17

Synthesis of PNA Oligomer 1 (H$_2$N-G-A-T-p MR-G-A-C-G-C—CONH$_2$) (Method 2)

Lowering titer of solid phase support Following the solid phase tboc method previously reported by Koch et al. (Koch, T.; Hansen, H. F.; Andersen, P.; Larsen, T.; Batz, H. G.; Otteson, K.; Ørum, H. J. Peptide Res. 1997, 49, 80–88.), a condensation reaction was first carried out with MBHA solid phase support (50 mg) using cytosine PNA monomer unit (10.1 mg, 20 μmol), and HBTU (7.6 mg, 20 μmol) and DIEA (3.5 μL, 20 μmol) as the condensing agent, for 2 h at room temperature. Next, capping of unreacted amino groups was carried out three times using the capping reagent Ac$_2$O/pyridine/DMF (1/2/2) for 30 min at room temperature. Completion of the capping reaction was confirmed by ninhydrin reagent.

Design of base sequence recognition region After deprotecting the Boc group by a TFA treatment (95% TFA/5% m-cresol), a condensation reaction using guanine PNA monomer unit (7.7 mg, 20 μmol), and HBTU (7.6 mg, 20 μmol) and DIEA (3.5 μL, 20 μmol) as the condensing agent, was carried out on the MBHA for 30 min at room temperature. After confirming completion of the condensation reaction with ninhydrin reagent, capping of unreacted amino groups on the MBHA was carried out using the capping reagent Ac$_2$O/pyridine/DMF (1/25/25) for 5 min at room temperature. This process was repeated a further seven times using each PNA monomer unit (guanine 10.9 mg, adenine 10.6 mg, thymine 7.7 mg, cytosine 10.1 mg, and PNA precursor Fmoc-Gly-$^{Boc}$PNA-OH 10.0 mg).

Post-synthetic incorporation of photo-functional region After condensing all the units in succession, the Fmoc group was deprotected with a piperidine treatment (20% piperidine in DMF, room temperature, 3 min). The photoactive carboxylic acid derivative p-Methyl Red (10.8 mg, 40 µmol) was then condensed using HBTU (15.2 mg, 40 µmol) and DIEA (7.0 µL, 40 µmol) as the condensing agent, thereby incorporating the photoactive molecule into the target location.

Cleavage from support/purification Finally, cleavage from the solid phase support and deprotection of the Cbz group were carried out simultaneously using the cleavage reagent TFA/TFMSA/p-cresol/thioanisole (60/25/10/10). A gradient composed of A (0.05% TFA in water) and B (0.05% TFA in acetonitrile) was used for analytical and preparative HPLC: Time 0, 0% B. Time 50 min, 50% B (flow rate: 10 mL/min, detection: 260 nm). UV λmax (H$_2$O) 303, 548 (nm).

Example 18

Synthesis of PNA Oligomer 2 (H$_2$N-G-A-T-m MR-G-A-C-G-C—CONH$_2$) (Method 2)

Lowering titer of solid phase support Following the solid phase tboc method previously reported by Koch et al. (Koch, T.; Hansen, H. F.; Andersen, P.; Larsen, T.; Batz, H. G.; Otteson, K.; Ørum, H. J. Peptide Res. 1997, 49, 80–88.), a condensation reaction was first carried out with MBHA solid phase support (50 mg) using cytosine PNA monomer unit (10.1 mg, 20 µmol), and HBTU (7.6 mg, 20 µmol) and DIEA (3.5 µL, 20 µmol) as the condensing agent, for 2 h at room temperature. Next, capping of unreacted amino groups was carried out three times using the capping reagent Ac$_2$O/pyridine/DMF (1/2/2) for 30 min at room temperature. Completion of the capping reaction was confirmed by ninhydrin reagent.

Design of base sequence recognition region After deprotecting the Boc group by a TFA treatment (95% TFA/5% m-cresol), a condensation reaction using guanine PNA monomer unit (7.7 mg, 20 µmol), and HBTU (7.6 mg, 20 µmol) and DIEA (3.5 µL, 20 µmol) as the condensing agent, was carried out on the MBHA for 30 min at room temperature. After confirming completion of the condensation reaction with ninhydrin reagent, capping of unreacted amino groups on the MBHA was carried out using the capping reagent Ac$_2$O/pyridine/DMF (1/25/25) for 5 min at room temperature. This process was repeated a further seven times using each PNA monomer unit (guanine 10.9 mg, adenine 10.6 mg, thymine 7.7 mg, cytosine 10.1 mg, and PNA precursor Fmoc-Gly-$^{Boc}$PNA-OH 10.0 mg).

Post-synthetic incorporation of photo functional region After condensing all the units in succession, the Fmoc group was deprotected with a piperidine treatment (20% piperidine in DMF, room temperature, 3 min). The photoactive carboxylic acid derivative m-Methyl Red (10.8 mg, 40 µmol) was then condensed using HBTU (15.2 mg, 40 µmol) and DIEA (7.0 µL, 40 µmol) as the condensing agent, thereby incorporating the photoactive molecule into the target location.

Cleavage from support/purification Finally, cleavage from the solid phase support and deprotection of the Cbz group were carried out simultaneously using the cleavage reagent TFA/TFMSA/p-cresol/thioanisole (60/25/10/10). A gradient composed of A (0.05% TFA in water) and B (0.05% TFA in acetonitrile) was used for analytical and preparative HPLC: Time 0, 0% B. Time 50 min, 50% B (flow rate: 10 mL/min, detection: 260 nm). UV λmax (H$_2$O) 308, 570 (nm).

Example 19

Synthesis of PNA Oligomer 3 (H$_2$N-G-A-T-o MR-G-A-C G-C—CONH$_2$) (Method 2)

Lowering titer of solid phase support Following the solid phase tBoc method previously reported by Koch et al. (Koch, T.; Hansen, H. F.; Andersen, P.; Larsen, T.; Batz, H. G.; Otteson, K.; Ørum, H. J. Peptide Res. 1997, 49, 80–88.), a condensation reaction was first carried out with MBHA solid phase support (50 mg) using cytosine PNA monomer unit (10.1 mg, 20 µmol), and HBTU (.7.6 mg, 20 µmol) and DIEA (3.5 µL, 20 µmol) as the condensing agent, for 2 h at room temperature. Next, capping of unreacted amino groups was carried out three times using the capping reagent Ac$_2$O/pyridine/DMF (1/2/2) for 30 min at room temperature. Completion of the capping reaction was confirmed by ninhydrin reagent.

Design of base sequence recognition region After deprotecting the Boc group by a TFA treatment (95% TFA/5% m-cresol), a condensation reaction using guanine PNA monomer unit (7.7 mg, 20 µmol), and HBTU (7.6 mg, 20 µmol) and DIEA (3.5 µL, 20 µmol) as the condensing agent, was carried out on the MBHA for 30 min at room temperature. After confirming completion of the condensation reaction with ninhydrin reagent, capping of unreacted amino groups on the MBHA was carried out using the capping reagent Ac$_2$O/pyridine/DMF (1/25/25) for 5 min at room temperature. This process was repeated a further seven times using each PNA monomer unit (guanine 10.9 mg, adenine 10.6 mg, thymine 7.7 mg, cytosine 10.1 mg, and PNA precursor Fmoc-Gly-$^{Boc}$PNA-OH 10.0 mg).

Post-synthetic incorporation of photo-functional region After condensing all the units in succession, the Fmoc group was deprotected with a piperidine treatment (20% piperidine in DMF, room temperature, 3 min). The photoactive carboxylic acid derivative o-Methyl Red (10.8 mg, 40 µmol) was then condensed using HBTU (15.2 mg, 40 µmol) and DIEA (7.0 µL, 40 µmol) as the condensing agent, thereby incorporating the photoactive molecule into the target location.

Cleavage from support/purification Finally, cleavage from the solid phase support and deprotection of the Cbz group were carried out simultaneously using the cleavage reagent TFA/TFMSA/p-cresol/thioanisole (60/25/10/10). A gradient composed of A (0.05% TFA in water) and B (0.05% TFA in acetonitrile) was used for analytical and preparative HPLC: Time 0, 0% B. Time 50 min, 50% B (flow rate: 10 mL/min, detection: 260 nm). UV λmax (H$_2$O) 302, 561 (nm).

Example 20

Synthesis of fluorescent PNA probe 1 incorporating membrane permeability

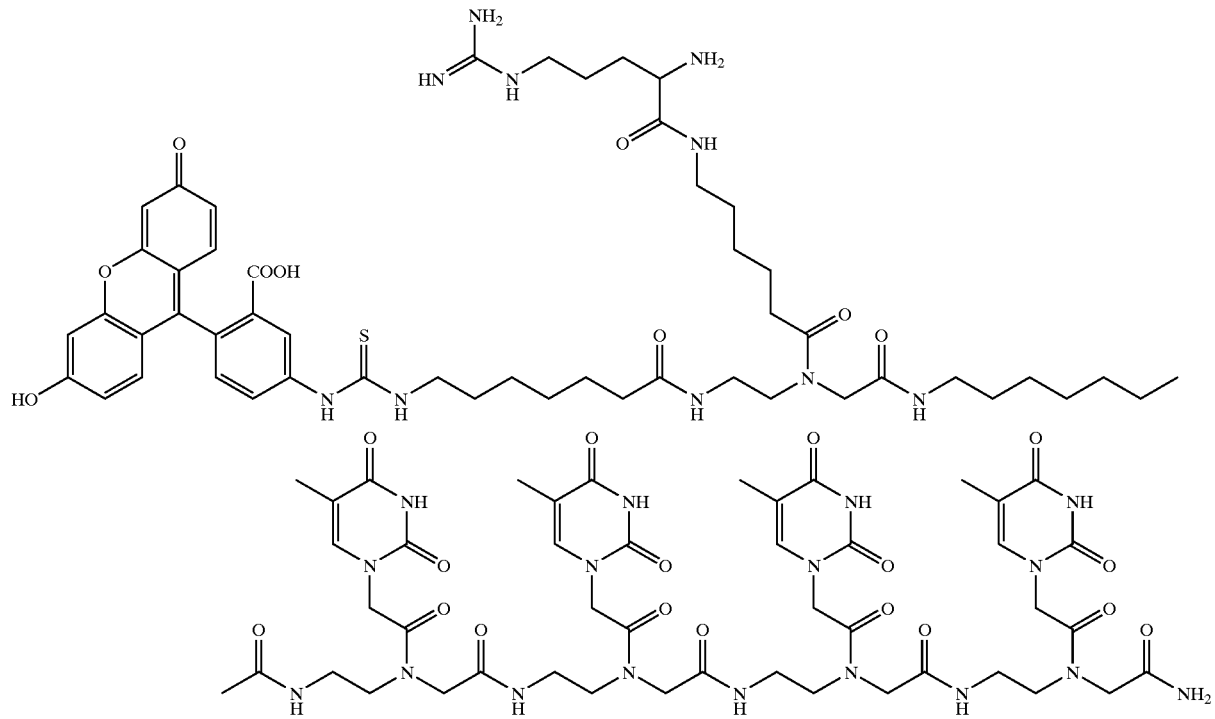

Compound 31 was synthesized according to Method 2 described above.

Lowering titer of solid phase support Following the solid phase tBoc method previously reported by Koch et al. (Koch, T.; Hansen, H. F.; Andersen, P.; Larsen, T.; Batz, H. G.; Otteson, K.; Ørum, H. J. Peptide Res. 1997, 49, 80–88.), a condensation reaction was first carried out with MBHA solid phase support (50 mg) using thymine PNA monomer unit (7.7 mg, 20 µmol), and HBTU (7.6 mg, 20 µmol) and DIEA (3.5 µL, 20 µmol) as the condensing agent, for 2 h at room temperature. Next, capping of unreacted amino groups was carried out three times using the capping reagent $Ac_2O$/pyridine/DMF (1/2/2) for 30 min at room temperature. Completion of the capping reaction was confirmed by ninhydrin reagent.

Design of base sequence recognition region After deprotecting the Boc group by a TFA treatment (95% TFA/5% m-cresol), a condensation reaction using thymine PNA monomer unit (7.7 mg, 20 µmol), and HBTU (7.6 mg, 20 µmol) and DIEA (3.5 µL, 20 µmol) as the condensing agent, was carried out on the MBHA for 30 min at room temperature. After confirming completion of the condensation reaction with ninhydrin reagent, capping of unreacted amino groups on the MBHA was carried out using the capping reagent $Ac_2O$/pyridine/DMF (1/25/25) for 5 min at room temperature. This process was repeated a further two times.

Design of linker site and membrane permeability functional region The ω-amino acid linker Boc-7-aminoheptanoic acid (5.2 mg, 20 µmol), the PNA precursor monomer unit Fmoc-C5-$^{Boc}$PNA-BH (10.0 mg, 20 µmol), and then again Boc-7-aminoheptanoic acid were condensed in succession using HBTU (7.6 mg, 20 µmol) and DIEA (3.5 µL, 20 µmol). Progress of the reaction was confirmed using ninhydrin reagent.

Post-synthetic incorporation of membrane permeability functionality molecule After condensing all the units in succession, the Fmoc group was deprotected with a piperidine treatment (20% piperidine in DMF, room temperature, 3 min). The functional carboxylic acid derivative Fmoc-Arg (Mts)-OH (23.1 mg, 40 µmol) was then condensed using HBTU (15.2 mg, 40 µmol) and DIEA (7.0 µL, 40 µmol) as the condensing agent, thereby incorporating the functional molecule into the target location.

Fluorescent labeling of PNA oligomer After deprotecting the Boc group with a TFA treatment (95% TFA/5% m-cresol), fluorescent labeling was carried out with FITC (9.3 mg, 25 µmol) in the presence of DIEA (17.4 µL, 100 µmol) by shaking at room temperature for 12 h.

Deprotection of Fmoc group and cleavage from support/purification Finally, after deprotecting the remaining Fmoc group with piperidine (50% piperidine in DMF, room temperature, 3 min), cleavage from the solid phase support and deprotection of the Cbz group were carried out simultaneously using the cleavage reagent TFA/TFMSA/p-cresol/thioanisole (60/25/10/10). A gradient composed of A (0.05% TFA in water) and B (0.05% TFA in acetonitrile) was used for analytical and preparative HPLC: Time 0, 0% B. Time 50 min, 50% B (flow rate: 10 mL/min, detection: 260 nm). The purified compound 31 was identified by MALDI-TOF MS. Calcd. 2096.26 $(M+H^+)$, found 2096.36.

Example 21

Synthesis of fluorescent PNA probe 2 incorporating membrane permeability.

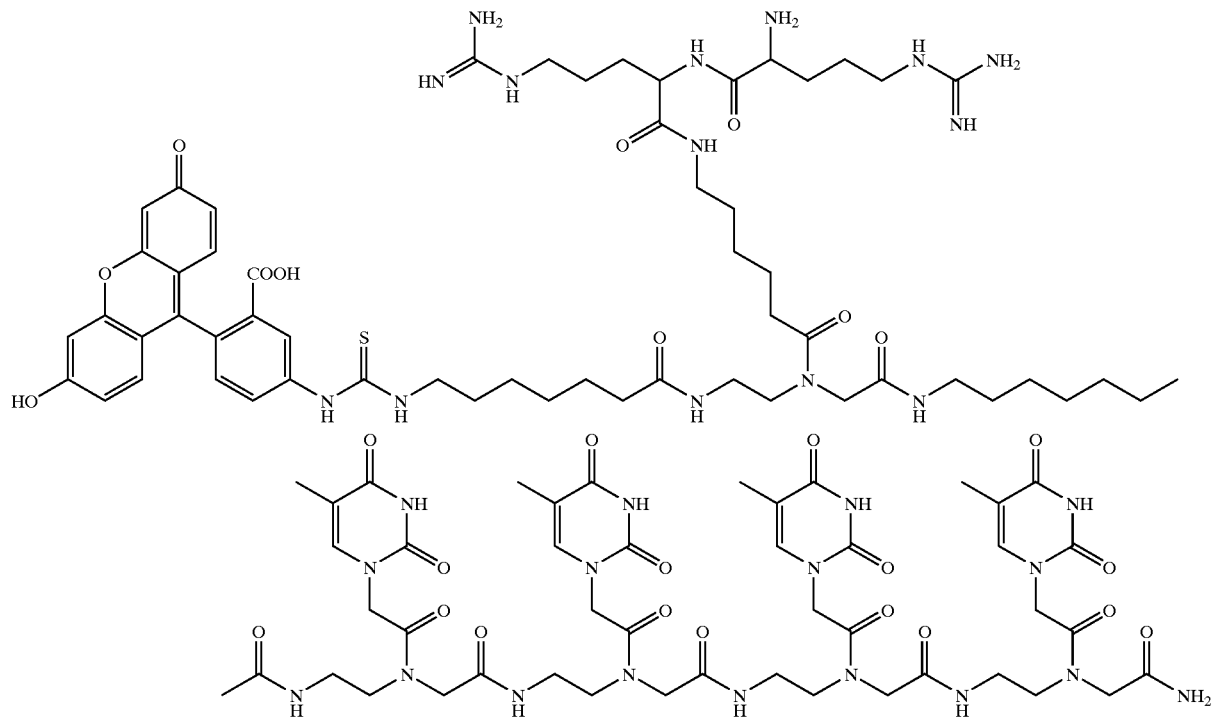

Reaction was carried out in the same way as for compound 31 up to the post synthetic incorporation of the functional molecule.

Lowering titer of solid phase support Following the solid phase tBoc method previously reported by Koch et al. (Koch, T.; Hansen, H. F.; Andersen, P.; Larsen, T.; Batz, H. G.; Otteson, K.; Ørum, H. J. Peptide Res. 1997, 49, 80–88.), a condensation reaction was first carried out with MBHA solid phase support (50 mg) using thymine PNA monomer unit (7.7 mg, 20 μmol), and HBTU (7.6 mg, 20 μmol) and DIEA (3.5 μL, 20 μmol) as the condensing agent, for 2 h at room temperature. Next, capping of unreacted amino groups was carried out three times using the capping reagent Ac$_2$O/pyridine/DMF (1/2/2) for 30 min at room temperature. Completion of the capping reaction was confirmed by ninhydrin reagent.

Design of base sequence recognition region After deprotecting the Boc group by a TFA treatment (95% TFA/5% m-cresol), a condensation reaction using thymine PNA monomer unit (7.7 mg, 20 μmol), and HBTU (7.6 mg, 20 μmol) and DIEA (3.5 μL; 20 μmol) as the condensing agent, was carried out on the MBHA for 30 min at room temperature. After confirming completion of the condensation reaction with ninhydrin reagent, capping of unreacted amino groups on the MBHA was carried out using the capping reagent Ac$_2$O/pyridine/DMF (1/25/25) for 5 min at room temperature. This process was repeated a further two times.

Design of linker site and membrane permeability functional region The ω-amino acid linker Boc-7-aminoheptanoic acid (5.2 mg, 20 ωmol), the PNA precursor monomer unit Fmoc-C5-$^{Boc}$PNA-OH (10.0 mg, 20 μmol), and then again Boc-7-aminoheptanoic acid were condensed in succession using HBTU (7.6 mg, 20 μmol) and DIEA (3.5 μL, 20 μmol). Progress of the reaction was confirmed using ninhydrin reagent.

Post-synthetic incorporation of membrane permeability functionality molecule After condensing all the units in succession, the Fmoc group was deprotected with a piperidine treatment (20% piperidine in DMF, room temperature, 3 min). The functional carboxylic acid derivative Fmoc-Arg (Mts)-OH (23.1 mg, 40 μmol) was then condensed using HBTU (15.2 mg, 40 μmol) and DIEA (7.0 μL, 40 μmol) as the condensing agent, thereby incorporating the functional molecule into the target location.

Incorporation of an orthogonal functional molecule: Additional incorporation of membrane permeability function After treating again with piperidine (50% piperidine in DMF, room temperature, 3 min) to deprotect the Fmoc group, Fmoc-Arg(Mts)-OH (23.1 mg, 40 μmol) was condensed using HBTU (15.2 mg, 40 μmol) and DIEA (7.0 μL, 40 μmol) as the condensing agent.

Fluorescent labeling of PNA oligomer After deprotecting the Boc group with a TFA treatment (95% TFA/5% m-cresol) fluorescent labeling was carried out with FITC (9.3 mg, 25 μmol) in the presence of DIEA (17.4 μL, 100 μmol) by shaking at room temperature for 12 h.

Deprotection of Fmoc groups and cleavage from support/purification Finally, after deprotecting the remaining Fmoc group with piperidine (50% piperidine in DMF, room temperature, 3 min), cleavage from the solid phase support and deprotection of the Cbz group were carried out simultaneously using TFA/TFMSA/p-cresol/thioanisole (60/25/10/10) as the cleavage reagent. A gradient composed of A (0.05% TFA in water) and B (0.05% TFA in acetonitrile) was used for analytical and preparative HPLC: Time 0, 0% B. Time 50 min, 50% B (flow rate: 10 mL/min, detection: 260 nm). Purified compound 32 was identified by MALDI-TOF MS. Calcd. 2252.44 (M+H$^+$), found 2252.33.

Effects of the Invention

According to this invention, it is possible to easily introduce manifold functional molecules containing the photoactive molecules into PNAs, it is possible to efficiently and easily introduce multiple functional molecules into the identical PNA, and it is possible to design-various PNAs for gene therapies, etc.

What is claimed is:

1. A method for producing a functional PNA oligomer; wherein a PNA monomer unit having adenine, guanine, cytosine or thymine protected by a protecting group is reacted with Fmoc-ω-amino acid-$^{Boc}$PNA-OH represented by the following general formula (I):

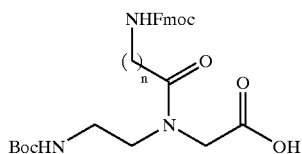

(wherein n represents a plus integer) and after synthesizing PNA oligomer, a functional molecule having free carboxylic acid is introduced into said PNA oligomer followed by deprotecting of the protecting group.

2. The method according to claim 1, wherein the Fmoc-ω-amino acid-$^{Boc}$PNA-OH is produced by a reaction between Fmoc-ω-amino acid pentafluorophenyl ester and $^{Boc}$PNA-OH.

3. The method according to claim 2, wherein the Fmoc-ω-amino acid pentafluorophenyl ester is produced by a reaction between Fmoc-ω-amino acid and pentafluorophenol.

4. The method according to claim 1, wherein there are plurality of said functional molecules, and every functional molecule is different from each other.

5. The method according to claim 1, wherein the introduced functional molecule is chosen from a photofunctional molecule, a membrane-permeable functional molecule, an organ-selective functional molecule, a bactericidal functional molecule and a molecule-recognizing functional molecule.

6. The method according to claim 4, wherein each functional molecule is chosen from a photofunctional molecule and a membrane-permeable functional molecule.

7. The method according to claim 6 wherein, the photofunctional molecule is FITC, ROX, TAMRA or Dabcyl, and the membrane-permeable functional molecule is a water-soluble amino acid.

8. The method according to claim 1, wherein the protecting group that protects adenine, guanine, cytosine or thymine is a N-benzyloxycarbonyl group.

9. The method according to claim 1, wherein synthesis of PNA oligomer contains condensation and elongation in a PNA chain using a solid-phase carrier for a tBoc method.

10. The method according to claim 9, wherein the solid-phase carrier for the tBoc method is methylbenzhydrylamine resin.

11. The method according to claim 1, wherein introduction of a functional molecule having free carboxylic acid is carried out by dehydration condensation with a primary amino group obtained by selectively deprotecting the Fmoc group by piperidine treatment.

12. The method according to claim 11, wherein Fmoc-ω-amino acid-$^{Boc}$PNA-OH is a compound represented by the following general formula (I):

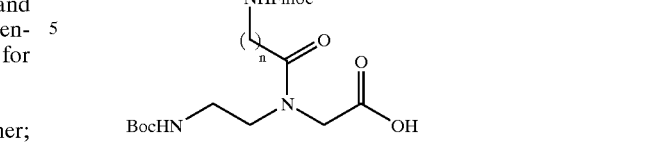

(wherein n represents an integer of 1 through 15).

13. The method according to claim 3, comprising one or more of the following steps a) through d) of:

a) reacting Fmoc-ω-amino acid and pentafluorophenol in a step in which Fmoc-ω-amino acid pentafluorophenylester is produced;

b) introducing Fmoc-ω-amino acid into $^{Boc}$PNA-OH by reacting Fmoc-ω-amino acid pentafluorophenyl ester with $^{Boc}$PNA-OH in a step in which Fmoc-ω-amino acid-$^{Boc}$PNA-OH is produced;

c) producing PNA oligomer by reacting a PNA monomer unit with Fmoc-ω-amino-acid-$^{Boc}$PNA-OH in a step in which PNA oligomer is produced from Fmoc-ω-amino acid-$^{Boc}$PNA-OH; and, d) carrying out introduction of a functional molecule into PNA oligomer by dehydration condensation of a primary amino group obtained by selectively deprotecting an Fmoc group by piperidine treatment in a step in which a functional PNA oligomer is produced from the said PNA oligomer.

14. A compound represented by the following general formula (I):

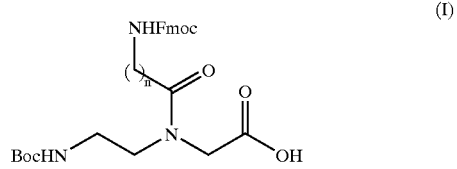

(wherein n represents an integer 1 through 15).

15. A method for producing a compound represented by the general formula (I):

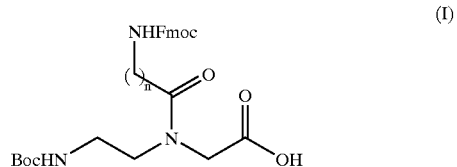

(wherein n represents an integer of 1 through 15) comprising the introduction of Fmoc-ω-amino acid by reacting Fmoc-ω-amino acid with pentafluorophenol, and reacting that reaction produce with $^{Boc}$PNA-OH.

16. A compound represented by general formula (II):

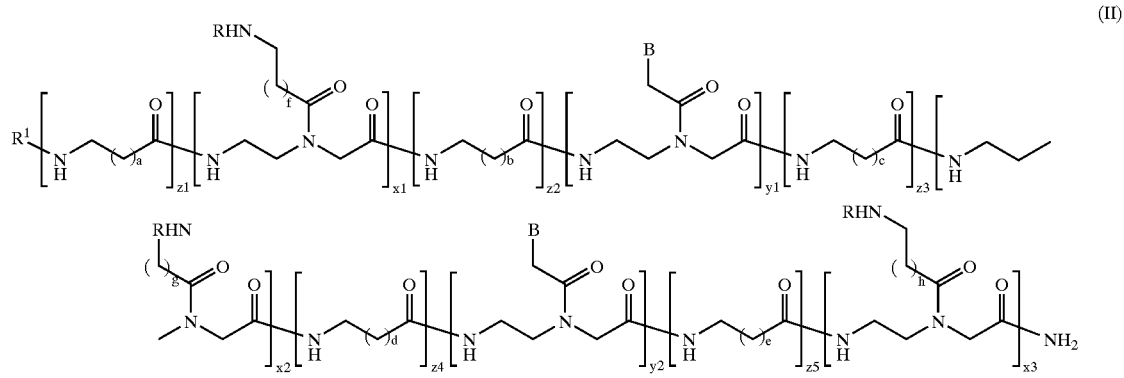

(wherein B's each independently are the same or different and represent adenine, guanine, cytosine or thymine, R's each independently are the same or different and represent an Fmoc group or a functional carboxylic acid derivative, $R^1$ represents a hydrogen atom or a functional carboxylic acid derivative, a through h represent integers of 0 to 10, $X_1$ through $X_3$, $Y_1$, $Y_2$, and $Z_1$ through $Z_5$ all represent integers of 0 or more, $X_1+X_2+X_3 \geq 0$, $Y_1+Y_2>0$, and $Z_1+Z_2+Z_3+Z_4+Z_5 \geq 0$, provided that $X_1+X_2+X_3$ and $Z_1+Z_2+Z_3+Z_4+Z_5$ are not simultaneously 0, and in the case where $X_1+X_2+X_3=0$, $R^1$ is a functional carboxylic acid derivative).

17. The compound according to claim 16, wherein $Z_1+Z_2+Z_3+Z_4+Z_5=0$, and $R^1$ is a hydrogen atom.

18. A compound according to claim 17, wherein R includes a carboxylic acid derivative of methyl red.

19. The compound according to claim 19, wherein $X_1+X_2+X_3=9$, and $Y_1+Y_2=1$.

20. The compound according to claim 19, wherein $X_1=3$, $X_2=6$ and $Y_1=1$.

21. The compound according to claim 16, wherein R or $R^1$ represents a cell membrane-permeable functional molecule derivative.

22. The compound according to claim 21, wherein $R^1$ represents a functional carboxylic acid derivative.

23. The compound according to claim 21, wherein $X_1=Z_1=1$.

24. The compound according to claim 21, wherein $Y_1 \geq 2$ and $Z_2-1$.

25. The compound according to claim 21, wherein $a \leq 6$, $b \leq 4$, and $f \leq 6$.

26. The compound according to claim 21, wherein $R^1$ is a photofunctional carboxylic acid derivative.

* * * * *

UNITED STATES PATENT AND TRADEMARK OFFICE
CERTIFICATE OF CORRECTION

PATENT NO. : 6,809,190 B2
DATED : October 26, 2004
INVENTOR(S) : Hisafumi Ikeda et al.

It is certified that error appears in the above-identified patent and that said Letters Patent is hereby corrected as shown below:

<u>Title page,</u>
Item [30], Foreign Application Priority Data, insert as follows:
-- 2002-121667 (JAPAN)   04-24-2002 --.

Signed and Sealed this

Fifteenth Day of February, 2005

JON W. DUDAS
*Director of the United States Patent and Trademark Office*